United States Patent
Gelbfish

[11] Patent Number: 5,928,218
[45] Date of Patent: Jul. 27, 1999

[54] MEDICAL MATERIAL REMOVAL METHOD AND ASSOCIATED INSTRUMENTATION

[76] Inventor: Gary A. Gelbfish, 2502 Avenue I, Brooklyn, N.Y. 11210

[21] Appl. No.: 08/653,514

[22] Filed: May 24, 1996

Related U.S. Application Data

[63] Continuation-in-part of application No. 08/573,323, Dec. 15, 1995, Pat. No. 5,730,717, which is a continuation-in-part of application No. 08/358,209, Dec. 16, 1994, Pat. No. 5,520,635.

[51] Int. Cl.$^6$ ........................................................ A61M 1/00
[52] U.S. Cl. ............................ 604/540; 604/164; 604/22; 606/159; 606/171
[58] Field of Search .................................. 604/21, 22, 28, 604/30, 49, 52, 93, 164, 246, 256, 264, 268, 280, 53, 96, 540; 606/167, 170, 171, 159; 600/564, 568

[56] References Cited

U.S. PATENT DOCUMENTS

| | | |
|---|---|---|
| 3,693,613 | 9/1972 | Kelman . |
| 3,844,272 | 10/1974 | Banko . |
| 3,882,872 | 5/1975 | Douves et al. . |
| 3,912,168 | 10/1975 | Mullins et al. . |
| 3,945,375 | 3/1976 | Banko . |
| 3,993,054 | 11/1976 | Newman . |
| 4,167,943 | 9/1979 | Banko . |
| 4,167,944 | 9/1979 | Banko . |
| 4,203,444 | 5/1980 | Bonnell et al. . |

(List continued on next page.)

FOREIGN PATENT DOCUMENTS

| | | |
|---|---|---|
| 1069398 | 5/1967 | United Kingdom . |
| 2018601 | 10/1978 | United Kingdom . |

OTHER PUBLICATIONS

Drasler et al., "Rheolytic Catheter for Percutaneous Removal of Thrombus," *Radiology,* 1992; 182:263–267.
"Introducing the AngioJet" brochure, 1993, Possis Medical Inc., Minneapolis, MN.

*Primary Examiner*—Corrine McDermott
*Assistant Examiner*—Cris L. Rodriguez
*Attorney, Agent, or Firm*—R. Neil Sudol; Henry D. Coleman

[57] ABSTRACT

A minimally invasive medical device comprises a tubular member with a large-diameter distal end portion and a smaller-diameter proximal portion. A clot-intake port is disposed in the distal end portion of the tubular member, while a cutter element is movably disposed in the distal end portion for severing material sucked in through the intake port and for temporarily closing the intake port during an extraction of the severed material from the device. A hollow drive rod extends through the tubular member to the cutter element for shifting the cutter element, while an outlet port is disposed in the tubular member proximally of the intake port and distally of the proximal portion of the tubular member. The tubular member extends through a catheter so that the intake port is disposed outside the catheter and the outlet port is disposed inside the catheter. The maximum transverse dimension of the proximal portion of the tubular member is substantially narrower than the lumen of the catheter, thereby providing flexibility to the combination of catheter and tubular drive element. A wire valve in the distal end portion of the tubular member is closed to block irrigation fluid from leaving an irrigation outlet in the drive rod while a mass is sucked into the tubular member through the intake port and is opened to permit flow of fluid when a severed mass is being sucked in a proximal direction through the catheter. A balloon at the distal end of the tubular member is inflated via irrigation fluid regulated by a valve operated according to the position of the cutter element.

10 Claims, 8 Drawing Sheets

U.S. PATENT DOCUMENTS

| | | |
|---|---|---|
| 4,428,748 | 1/1984 | Peyman et al. . |
| 4,493,694 | 1/1985 | Wuchinich . |
| 4,516,398 | 5/1985 | Wuchinich . |
| 4,555,645 | 11/1985 | Atkinson . |
| 4,589,412 | 5/1986 | Kensey . |
| 4,604,089 | 8/1986 | Santangelo et al. . |
| 4,631,052 | 12/1986 | Kensey . |
| 4,634,420 | 1/1987 | Spinosa et al. . |
| 4,646,736 | 3/1987 | Auth . |
| 4,669,469 | 6/1987 | Gifford, III et al. . |
| 4,670,006 | 6/1987 | Sinnett et al. . |
| 4,678,459 | 7/1987 | Onik et al. . |
| 4,679,596 | 7/1987 | Olson . |
| 4,690,672 | 9/1987 | Veltrup . |
| 4,692,139 | 9/1987 | Stiles . |
| 4,729,763 | 3/1988 | Henrie . |
| 4,770,654 | 9/1988 | Rogers et al. . |
| 4,790,813 | 12/1988 | Kensey ............ 604/22 |
| 4,846,192 | 7/1989 | MacDonald . |
| 4,857,045 | 8/1989 | Rydell . |
| 4,890,611 | 1/1990 | Monfort et al. . |
| 4,890,612 | 1/1990 | Kensey . |
| 4,895,166 | 1/1990 | Farr et al. . |
| 4,898,575 | 2/1990 | Fischell et al. . |
| 4,909,249 | 3/1990 | Akkas et al. . |
| 4,909,781 | 3/1990 | Husted . |
| 4,911,161 | 3/1990 | Schechter . |
| 4,913,698 | 4/1990 | Ito et al. . |
| 4,921,476 | 5/1990 | Wuchinich . |
| 4,926,858 | 5/1990 | Gifford, III et al. ............ 606/159 |
| 4,950,277 | 8/1990 | Farr . |
| 4,954,129 | 9/1990 | Giuliani et al. . |
| 4,966,604 | 10/1990 | Reiss . |
| 4,986,807 | 1/1991 | Farr . |
| 4,990,134 | 2/1991 | Auth . |
| 4,994,067 | 2/1991 | Summers . |
| 4,998,919 | 3/1991 | Schnapp-Pesch . |
| 5,002,553 | 3/1991 | Shiber . |
| 5,007,917 | 4/1991 | Evans . |
| 5,009,659 | 4/1991 | Hamlin et al. . |
| 5,011,488 | 4/1991 | Ginsburg . |
| 5,011,490 | 4/1991 | Fischell et al. . |
| 5,019,036 | 5/1991 | Stahl . |
| 5,019,088 | 5/1991 | Farr . |
| 5,030,201 | 7/1991 | Palestrant . |
| 5,042,984 | 8/1991 | Kensey et al. . |
| 5,052,999 | 10/1991 | Klein . |
| 5,069,224 | 12/1991 | Zinnanti . |
| 5,071,424 | 12/1991 | Reger . |
| 5,078,722 | 1/1992 | Stevens ............ 606/159 |
| 5,084,010 | 1/1992 | Plaia et al. ............ 604/22 |
| 5,084,052 | 1/1992 | Jacobs . |
| 5,092,838 | 3/1992 | Kipperman . |
| 5,092,839 | 3/1992 | Kipperman . |
| 5,100,424 | 3/1992 | Jang et al. . |
| 5,102,415 | 4/1992 | Guenther et al. . |
| 5,114,399 | 5/1992 | Kovalcheck . |
| 5,135,483 | 8/1992 | Wagner et al. . |
| 5,135,484 | 8/1992 | Wright . |
| 5,181,920 | 1/1993 | Mueller et al. ............ 606/159 |
| 5,192,268 | 3/1993 | Shiber . |
| 5,192,290 | 3/1993 | Hilal . |
| 5,192,291 | 3/1993 | Pannek, Jr. . |
| 5,242,404 | 9/1993 | Conley et al. . |
| 5,250,060 | 10/1993 | Carbo et al. ............ 606/159 |
| 5,250,065 | 10/1993 | Clement et al. ............ 606/172 |
| 5,261,877 | 11/1993 | Fine et al. . |
| 5,269,751 | 12/1993 | Kaliman et al. . |
| 5,284,472 | 2/1994 | Sussman et al. ............ 604/22 |
| 5,284,486 | 2/1994 | Kotula et al. . |
| 5,318,518 | 6/1994 | Plechinger et al. . |
| 5,322,504 | 6/1994 | Doherty et al. . |
| 5,342,377 | 8/1994 | Lazerson . |
| 5,348,535 | 9/1994 | Cucin . |
| 5,352,194 | 10/1994 | Greco et al. . |
| 5,356,375 | 10/1994 | Higley et al. . |
| 5,358,509 | 10/1994 | Fine et al. . |
| 5,370,609 | 12/1994 | Drasler et al. . |
| 5,370,653 | 12/1994 | Cragg . |
| 5,376,100 | 12/1994 | Lefebvre . |
| 5,395,313 | 3/1995 | Naves et al. . |
| 5,403,276 | 4/1995 | Schechter et al. . |
| 5,409,454 | 4/1995 | Fischell et al. ............ 604/22 |
| 5,419,774 | 5/1995 | Willard et al. . |
| 5,429,136 | 7/1995 | Milo et al. . |
| 5,431,673 | 7/1995 | Summers et al. . |
| 5,453,088 | 9/1995 | Boudewijn et al. . |
| 5,496,267 | 3/1996 | Drasler et al. ............ 604/22 |
| 5,569,277 | 10/1996 | Evans et al. ............ 606/159 |
| 5,685,840 | 11/1997 | Schechter et al. ............ 604/22 |

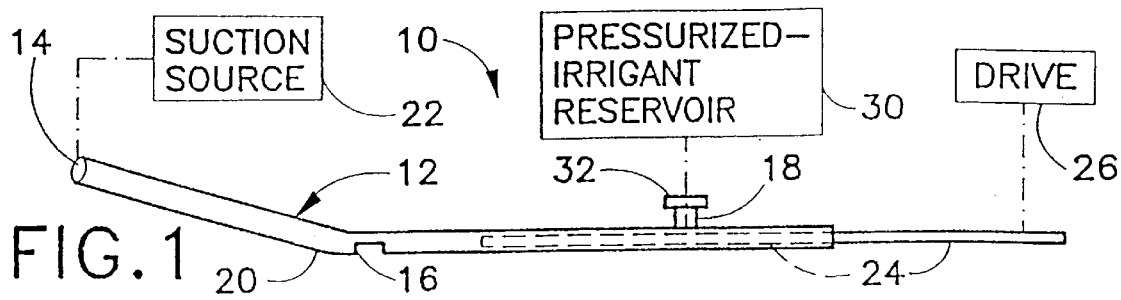
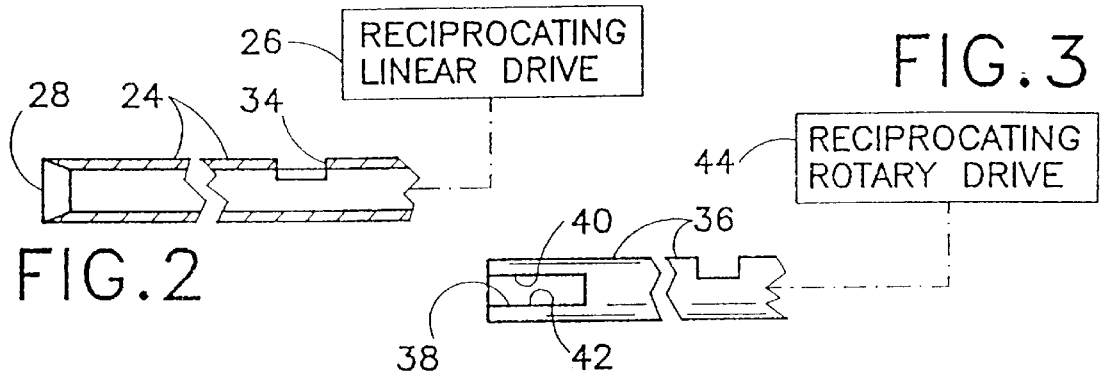
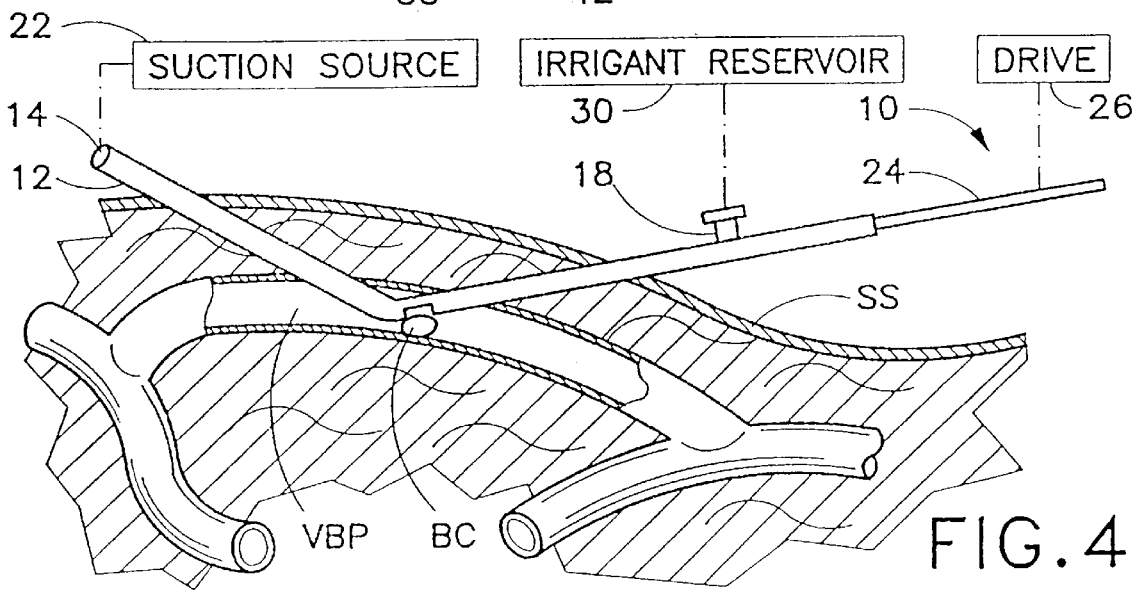
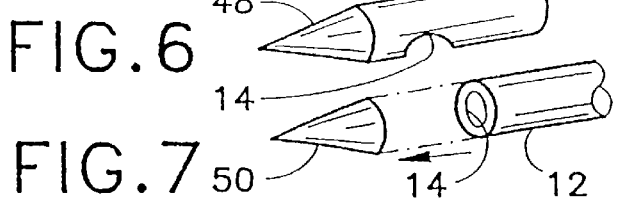
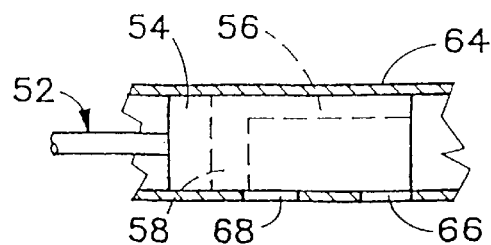

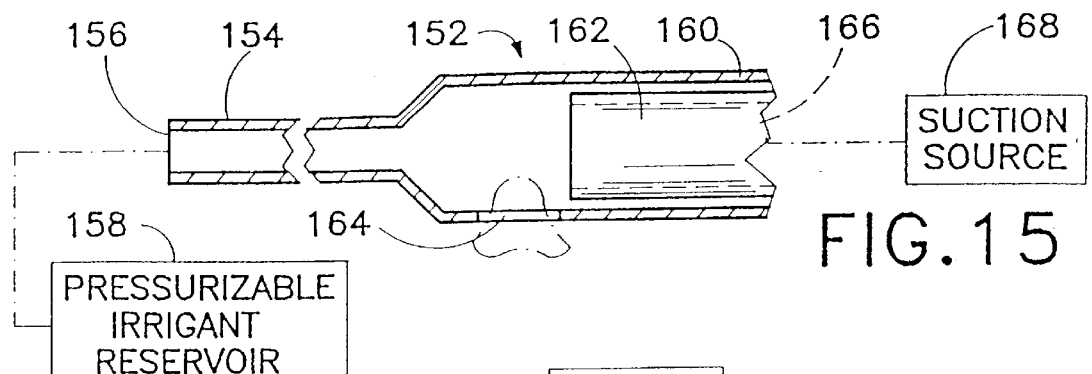
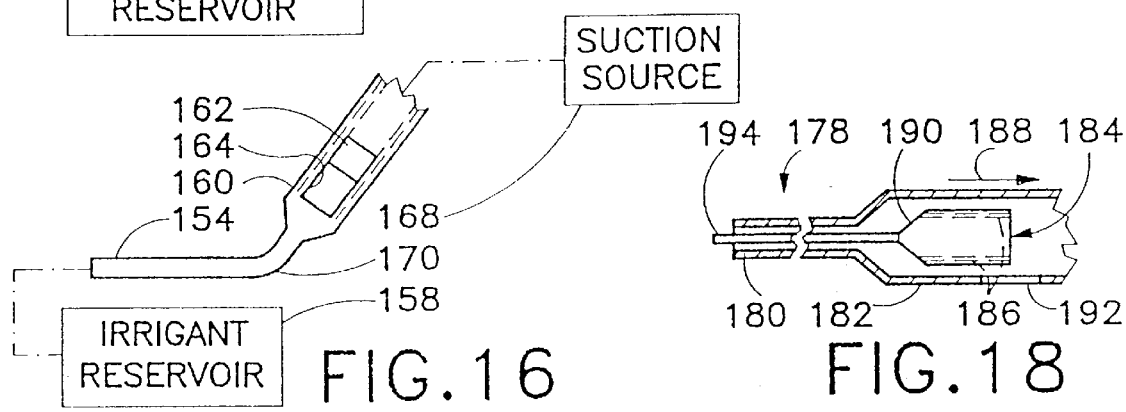
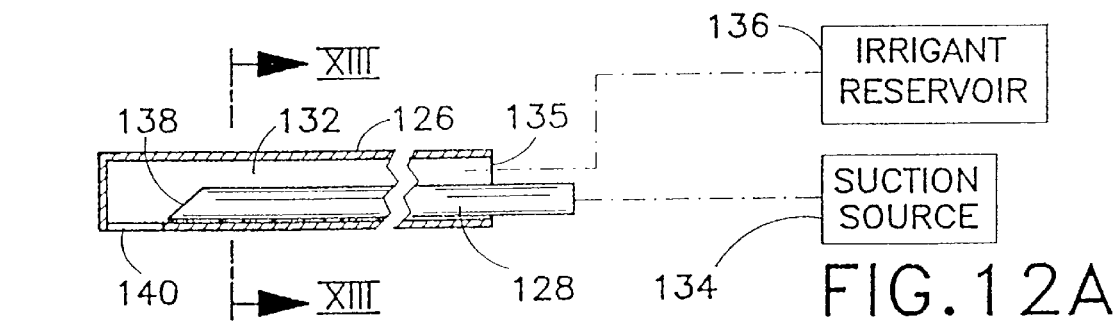
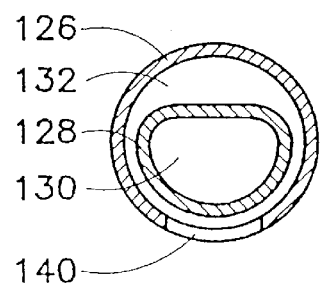
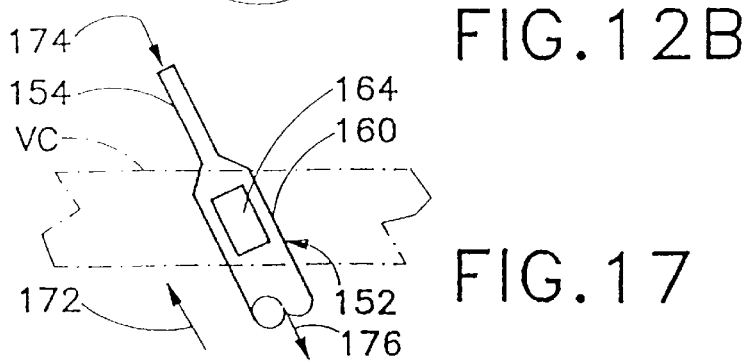

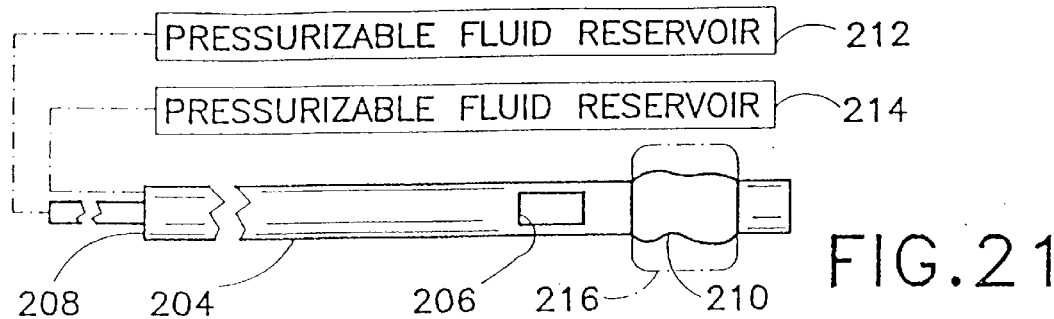
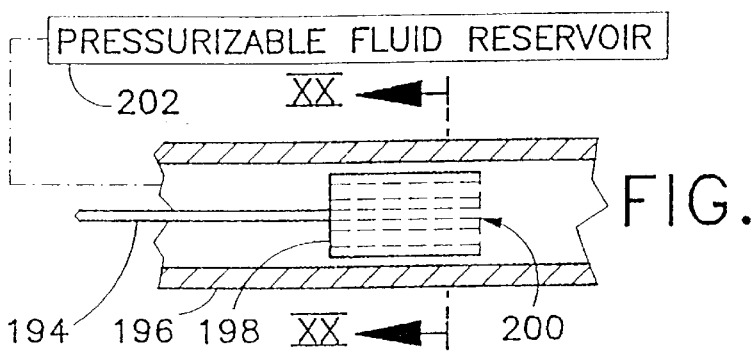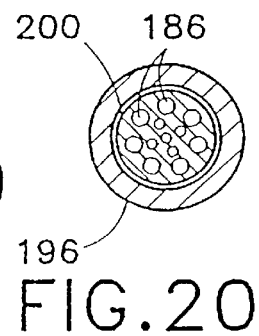
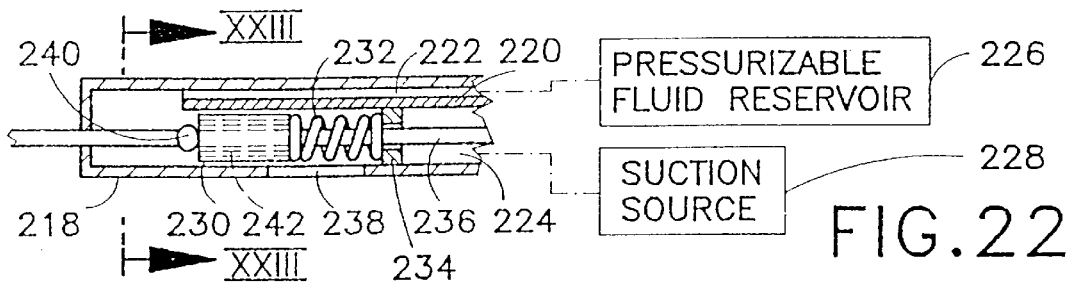
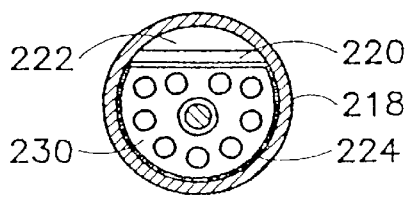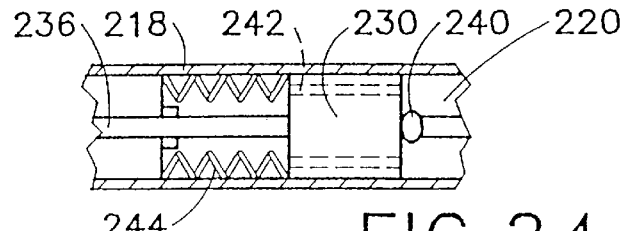
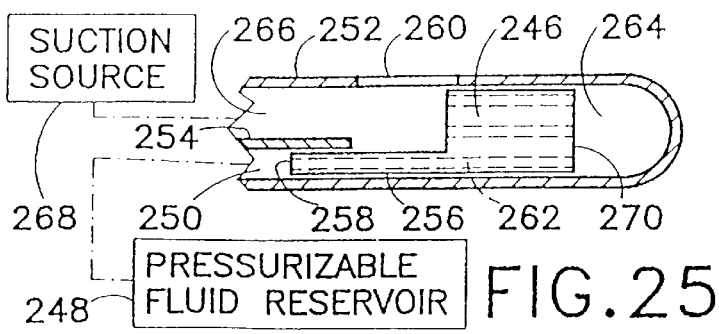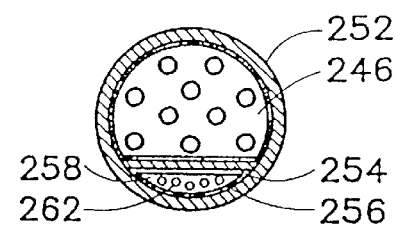

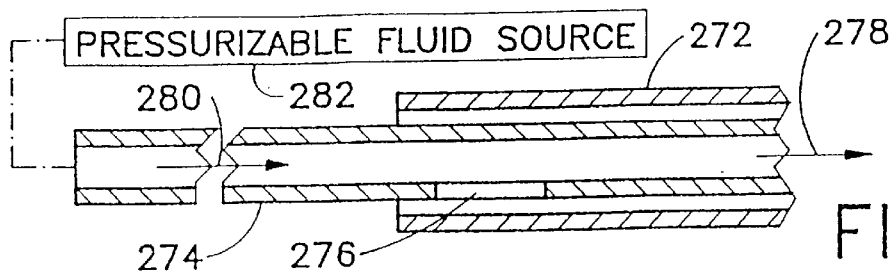
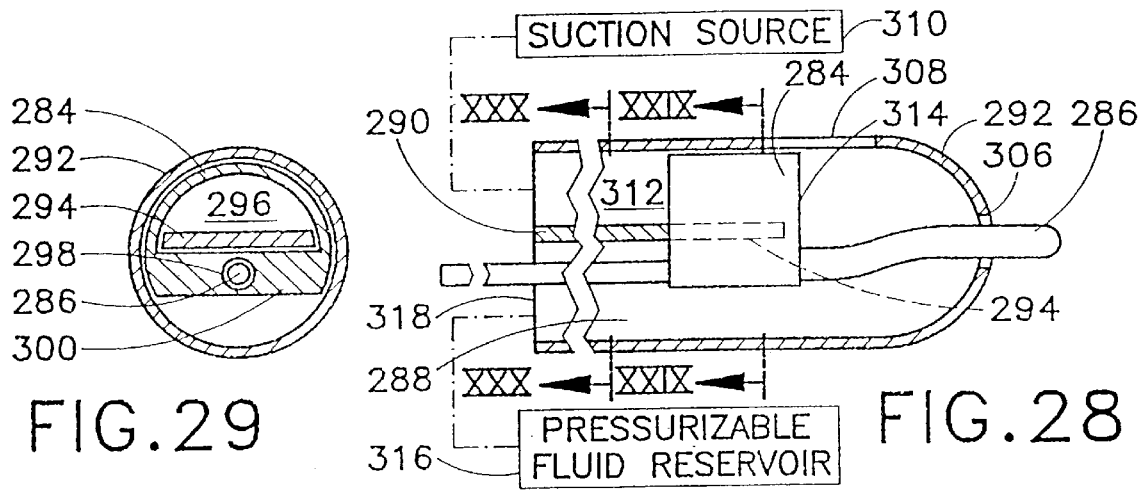
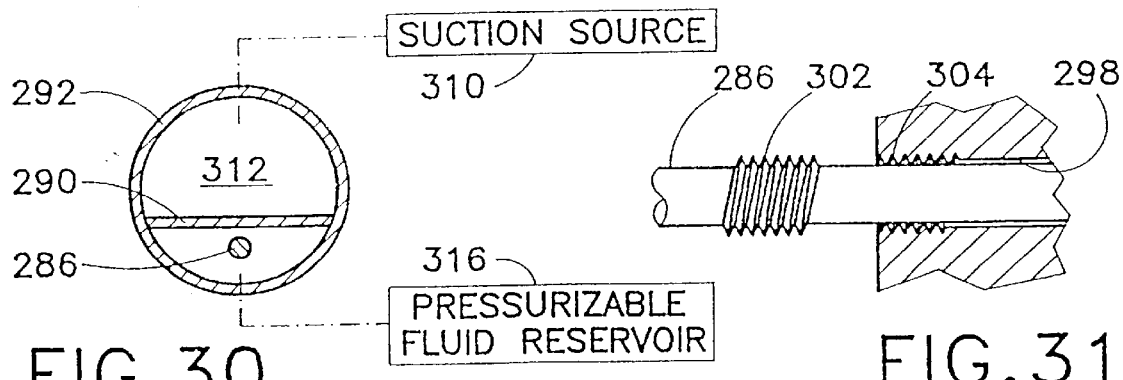
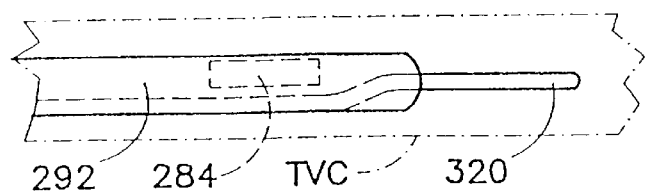
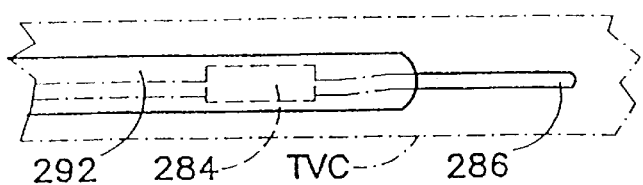

MEDICAL MATERIAL REMOVAL METHOD AND ASSOCIATED INSTRUMENTATION

CROSS-REFERENCE TO RELATED APPLICATION

This application is a continuation-in-part of application No. 08/573,323 filed Dec. 15, 1995, now U.S. Pat. No. 5,730,717 in turn a continuation-in-part of application No. 08/358,209 filed Dec. 16, 1994, now U.S. Pat. No. 5,520,635.

BACKGROUND OF THE INVENTION

This invention relates to a method and an associated device for obtaining access to internal organs, such as vascular components. More particularly, this invention relates to a method and an associated device for removing material internally from a patient. The method and the device are especially useful for removing clots from subcutaneous vascular bypasses or shunts.

Vascular bypasses, whether made of human tissue or polymeric material (graft), become regularly blocked with blood clots which must be removed. A common technique for cleaning clogged vascular bypasses is surgical: the skin surface and the underlying shunt are cut open and instruments are inserted through the openings to extract clumps of clotted blood.

The disadvantages of this conventional surgical procedure are well known. Because of the blood which naturally spurts out through the incision, the cleaning of the graft or bypass must be performed in the operating room. Of course, all the disadvantages or side-effects of surgery pertain: pain to the patient, danger of infection, loss of blood, as well as time and expense due to the requisite hospital staff.

Another common method of cleaning clogged vascular bypasses is dissolution of the clot via biological enzymes. The most common enzyme in current use is urokinase. The disadvantages of this method include high cost of the enzymes and a delay of as much as several hours while the enzyme acts on the clot. Systemic side effects of these enzymes, notably bleeding at other sites in the body due to unwanted yet uncontrolled dissolution of other "good" clots, are also seen.

Because of the limitations of surgical and enzymatic treatment, a myriad of other methods has been proposed to remove clot. The most intuitive method is clot removal via a suction catheter. Indeed this was first reported by Handley in 1907 in the British Medical Journal in a patient with clot at the bifurcation of the aorta. In his case report, a suction catheter was threaded upwards through a groin incision, but failed to remove significant amounts of clot. It was subsequently necessary to employ mechanical maceration and forcible saline irrigation in conjunction with the native aortic pressure to expel the clot and restore flow.

More recently, the use of suction thrombectomy has been reported in the medical literature, where large bore catheters (8–10 Fr.) are introduced and suction is applied to suck clot from the body. This technique has been revived by some vascular interventionalists as described in a few case reports. It has been used in areas where small amounts of clot can have critical consequences, such as the coronary arteries of the heart and pre-morbid patients with massive pulmonary embolism. Unfortunately, these catheters leave large and potentially damaging holes in the body. Furthermore, even these large catheters need to be repetitively removed and flushed secondary to adherent and obstructing clot. Bleeding from the resulting holes is also a major problem. This method has very limited applicability in clinical medicine and has largely been abandoned in favor of other methods.

Many mechanical devices known as "thrombectomy devices" have been described in United States patents. These patents are too numerous to review individually but the following general concepts apply to all.

Mechanical devices operate by many proposed mechanisms, including rotating catheter caps, drill bits and abrasive heads, high speed enclosed rotors creating a vortex which pulls in and macerates clot, waterjets based on various principles and with various configurations, ultrasonic devices, rotating wires baskets, brushes and blades, etc. Clot is macerated via these externally powered devices into a fine particulate size so that it may be aspirated through small device channels or be better tolerated if left in the body. In some devices, irrigation fluid is introduced to form a slurry of macerated clot and fluid or the patient's blood is used for this purpose. This approach of energized clot maceration has been thought by previous inventors to be the only possible rapid mechanical solution to the thrombectomy problem, considering the physical limitations of removing unmodified clot via suction through small diameter tubes.

Another general limitation of previously described devices is that clot is processed externally to the device and the blood vessel is used as a containment vessel. This permits clot particles to escape into the general circulation (embolization). In addition, biochemical aberrations in the blood secondary to microscopic red blood cell disruption (lysis) is routinely seen with some devices.

Recently, instrumentation has been described in U.S. Pat. No. 5,419,774 to Willard et al. to remove thrombus. This device has multiple lumens including two irrigation channels, a suction channel and a solid drive shaft all terminating in a common chamber distally where a reciprocating cutting mechanism is located. The device functions by sucking clot into a tubular catheter member, severing the drawn-in clot material and supplying fluid to remove severed thrombus from the tubular member. A fluid flow path with saline irrigation may be set up internal and external to the device to decrease the chance of device clogging. In addition, the method disclosed in Willard includes a step where fluid is introduced into the vessel in order to dilute the thrombus and modify its consistency. Diluting fluid is fed to the clot in the vascular system through a hole in the catheter or between the catheter and a surrounding sheath. The need to perform these additional maneuvers and the device design illustrate the as-yet unsolved limitations even with recently proposed clot removal technology. For example, the introduction of fluid into a clotted vascular space is not desirable and possibly contraindicated in many clinical circumstances. Certainly in the ideal thrombectomy device, fluid infusion into the vessel lumen, or any other clot modification maneuvers should be unnecessary to accomplish clot removal.

As described, these previous devices collectively suffer one or more deficiencies including cost, mechanical complexity, large cross sectional diameter secondary to multiple channels and septa between the channels. In addition, embolization of clot and other safety concerns exist especially considering that significant amounts of energy must be transferred into the body, in order to accomplish clot modification. Because of these limitations, the search for the ideal thrombectomy device is still continuing.

It is to be noted that similar cutting instrumentation has been disclosed for use in atherectomy procedures. While these devices may appear to be similar to thrombectomy devices, atherectomy devices have not been used and are not generally applicable for use in thrombectomy procedures where the technical challenge is high volume clot removal and not the cutting of soft gelatinous clot. In atherectomy devices, the precise cutting of hard calcified and usually irregular and eccentric vessel-wall lesions is necessary under precise operator control, such that an exact amount of tissue is removed yet vessel perforation does not occur. The volume of removed substance is generally small and does not present a waste removal problem under most circumstances. Indeed the Simpson atherectomy catheter, which is the most commonly used atherectomy catheter in clinical use, has no waste removal capabilities and all debris is stored in the catheter tip, which may only be cleaned after the catheter is removed from the body.

Notwithstanding this basic difference in purpose between atherectomy and thrombectomy devices, multiple atherectomy catheters with irrigation channels to aid in debris removal exist. U.S. Pat. No. 4,846,192 to MacDonald is illustrative of this group. It describes a rearwardly acting surgical catheter. A centrally located drive shaft supplies irrigation fluid to the area of the cutting element via two opposing openings in the shaft. The design of this and other similarly functioning catheters that contain irrigation channels is such that tissue is cut into a small particulate size and fluid acts as a lubricant and as a carrier medium for the excised tissue to be washed away. Inspection of the mechanical characteristics and irrigation channel configuration of the MacDonald, Willard and other devices with similar capabilities will conclusively show that they are not designed for the repetitive and intentional clogging as a mechanism for debris removal nor can they generally tolerate such an occurrence without seriously impacting their performance. Indeed this occurrence must be avoided since a full obstruction of the catheter lumen suction channel and/or cutting chambers, would not be completely cleared via irrigation through their respective irrigation channels.

OBJECT OF THE INVENTION

A general object of the present invention is to provide an improved method and an associated device for removing material, such as clot, adipose tissue and intraocular material, from a patient.

A further object of the present invention is to provide such a method which reduces, if not eliminates, at least one or more disadvantages of conventional surgical or enzymatic clot removal techniques.

Yet another particular object of the present invention is to provide such a technique or method which reduces the time required to remove a subcutaneous vascular clot.

A further object of the present invention is to provide such a method which reduces if not eliminates one or more disadvantages of conventional surgical methods, enzymatic methods or those of other proposed percutaneous clot modification or extraction techniques.

Another object of this invention is to provide such a device that is mechanically simple and with low energy requirements, in order to decrease device cost, and the potential for mechanical failure and bodily harm.

BRIEF DESCRIPTION

A device in accordance with the present invention is designed to maximize the efficiency of clot removal through the smallest diameter tubes. It is further designed to minimize device complexity and cost, to minimize clot maceration and embolization and to obviate the need of drive motors or other high energy sources under most clinical circumstances.

To accomplish this goal, the broad strategy of clot removal proceeds as follows. A device is designed so as to maximize the unobstructed cross sectional diameter of the suction/waste lumen and to minimize the size and number of accessory lumens. A maximum segment of clot is entrapped via suction into the device, self limited by its viscosity and other physical characteristics until a substantially cylindrical clot mass completely fills and obstructs the suction/waste lumen. Once this occurs, a cutter that functions also as a closing shutter, severs the clot, thus closing and sealing the device and isolating the entrapped clot. This motion additionally shields the blood vessel from subsequently generated device irrigation and pressure. Strategically located suction and fluid irrigation apertures act with synergistic efficiency across the clot to move and eject the clot from the device to a waste receptacle outside the patient. The cycle is then repeated. Under most circumstances even the incremental effect of fluid under just atmospheric pressure is sufficient to effect clot removal considering that the clot has been severed and is no longer connected to a larger and as yet unprocessed mass of clot, and that the initial limitation for further clot aspiration into the device was the inability of suction alone to move the clot through the suction lumen of the device.

Laboratory bench testing with clot of various ages and consistencies, in addition to in vivo animal and human thrombectomy testing confirms that this novel and hitherto undescribed theory and mechanism of clot removal enables large volumes of clot to be easily removed through small bore tubes (15 gauge or smaller) with devices of simple construction. Conceptually each time a reciprocation is made and the device is cleared, it is functionally equivalent to the laborious removal of a traditional suction catheter from the body, cleansing it, reinserting and repositioning it within the body. This simple but effective thrombectomy system and catheter cleansing mechanism permits a revival, in a distinctly modern and efficient form, of the original and most intuitive method of clot removal first described yet discarded by Handley almost 90 years ago.

A minimally invasive medical device comprises, in accordance with an embodiment of the present invention, a tubular member having a distal end portion and a proximal portion, the proximal portion having a maximum outer transverse dimension smaller than a maximum outer transverse dimension of the distal end portion. The distal end portion of the tubular member is provided with an intake port, and the tubular member is further provided with an outlet port disposed proximally of the intake port and distally of the proximal portion of the tubular member. A cutter element is movably disposed in the tubular member, the cutter element having a cutting edge. A drive rod extends through the proximal portion of the tubular member and into the distal end portion thereof, the drive rod being connected at a distal end to the cutter element for moving the cutting edge of the cutter element past the intake port. The drive rod has a longitudinally extending first lumen provided with an irrigation outlet communicating with the lumen at a distal end thereof.

Preferably, the device described above is used with a catheter having a proximal end provided with a suction port communicating with the lumen of the catheter. The tubular member extends through the catheter so that the intake port is disposed outside the catheter and the outlet port is disposed inside the catheter. The maximum transverse dimension of the proximal portion of the tubular member is substantially narrower than the lumen of the catheter, thereby providing a maximal flexibility in the combination of the catheter and tubular material removal member. Also, the use of such as catheter, known as an introducer sheath, which is placed at the onset of a diagnostic procedure, economizes on material costs and decreases the number of tubes attached to the device.

In a minimally invasive method utilizing the above-described device, a distal end section of the catheter is inserted into a patient, for example, into a vascular component of the patient in a thrombectomy procedure. The tubular member is inserted into the catheter so that the intake port is disposed outside the catheter and the outlet port is disposed inside the catheter. The drive rod is shifted so that the cutter element moves to open the intake port, whereupon suction is applied to the catheter via the suction port to pull material from the patient through the intake opening into the distal end portion of the tubular member. The drive rod is then shifted to move the cutting edge past the intake port and to thereby sever the material pulled into the distal end portion of the tubular member. By an application of suction force, the severed material is drawn in a proximal direction from the distal end portion of the tubular member, through the outlet port and along the catheter, outside of the proximal portion of the tubular member, to the suction port of the catheter. During this drawing of the severed material, fluid is fed into the tubular member upstream of the severed material to facilitate the drawing of the severed material. This fluid serves to break the suction upstream of the severed material, thereby ensuring that a pressure differential continuously exists across the severed mass at all times and positions within the tubular member.

Preferably, the drive rod is hollow, for the feeding of the fluid to the tubular member through the drive rod to an irrigation port. The irrigation port is placed in a most distal position, either in the drive rod, the cutter element or an extension of the drive rod on a distal side of the cutter element, to ensure that the fluid feed always comes in upstream of a severed mass.

In another embodiment of the present invention, a valve is disposed in the tubular member for closing the irrigation outlet during a suctioning phase of an operating cycle and for opening the irrigation outlet after a proximally directed severing stroke of the cutting edge past the intake port. In one specific embodiment of the invention, the valve including a longitudinally extending wire connected to the tubular member at a distal end thereof, the wire extending into a channel provided in the cutter element, the channel being colinear with the lumen of the drive rod. In another specific embodiment of the invention, the valve includes a sleeve disposed on a distal side of the cutter element for receiving a tubular extension of the drive rod, the irrigation outlet being disposed in the extension. Thus, the irrigation outlet is automatically opened upon a shifting of the drive rod and therefore, the cutter element past a predetermined, fixed location relative to the tubular member. This easy regulation of irrigation ensures that irrigation fluid will not be inadvertently introduced into the patient and also economizes on irrigant volume so that it is only used to move clot.

In a further embodiment of the present invention, a balloon is attached to the tubular member at a distal end thereof. A one-way valve is provided at the distal end of the tubular member for preventing deflation of the balloon upon an inflation thereof. In addition, a valve opening component is connected to the cutter element for opening the one-way balloon valve upon a distally directed stroke of the cutter element. This embodiment of the invention is particularly effective in reducing the number of component parts by enabling inflation of the balloon via the drive rod and suction channels. A separate balloon inflation channel is not required, thus decreasing the overall cross-sectional diameter of the device.

In using the balloon, a pressurization fluid is fed to the distal end portion of the tubular member and through the one-way valve (which may be a self-sealing membrane) to the balloon. After inflation of the balloon, tension is exerted on the tubular member to pull the balloon through the vascular component into which the tubular member has been inserted. Subsequently, the cutter element is shifted in the distal direction to open the one-way valve and deflate the balloon.

BRIEF DESCRIPTION OF THE DRAWING

FIG. 1 is partially a schematic side elevational view and partially a block diagram of a device for removing a subcutaneous blood clot.

FIG. 2 is partially a schematic longitudinal cross-sectional view and partially a block diagram showing a cutting component of the device of FIG. 1.

FIG. 3 is partially a schematic side elevational view and partially a block diagram showing an alternative cutting component for the device of FIG. 1.

FIG. 4 is partially a schematic cross-sectional view of subcutaneous tissues and a vascular bypass and partially a schematic side elevational view of the device of FIG. 1, showing a step in an operation removing a clot in the bypass.

FIGS. 5–7 are schematic partial perspective views of respective alternative embodiments of the distal end of tubular member 12, on an enlarged scale.

FIG. 8 is a schematic partial cross-sectional view of a modified obturator.

FIG. 12A is partially a block diagram and partially a schematic partial longitudinal cross-sectional view, on an enlarged scale, of another thrombectomy device, showing the device in a clot intake phase of an operating cycle.

FIG. 12B is a view similar to FIG. 12A, showing the device of FIG. 12A upon completion of a cutting or macerating stroke.

FIG. 13 is a schematic cross-sectional view taken along line XIII—XIII in FIG. 12A.

FIG. 15 is partially a block diagram and partially a schematic partial longitudinal cross-sectional view, on an enlarged scale, of a further thrombectomy device.

FIG. 16 is a schematic side elevational view, on an enlarged scale, of a modification of the thrombectomy device of FIG. 15.

FIG. 17 is a diagram illustrating use of the thrombectomy device of FIG. 15 or 16.

FIG. 18 is a schematic partial longitudinal cross-sectional view, on an enlarged scale, of an additional thrombectomy device.

FIG. 19 is partially a block diagram and partially a schematic partial longitudinal cross-sectional view, on an enlarged scale, of a modified thrombectomy device.

FIG. 20 is a schematic transverse cross-sectional view taken along line XX—XX in FIG. 19.

FIG. 21 is schematic side elevational view, on an enlarged scale, of yet another thrombectomy device.

FIG. 22 is partially a block diagram and partially a schematic partial longitudinal cross-sectional view, on an enlarged scale, of yet another thrombectomy device.

FIG. 23 is a schematic transverse cross-sectional view taken along line XXIII—XXIII in FIG. 22.

FIG. 24 is a schematic partial longitudinal cross-sectional view showing a variation on the thrombectomy device of FIGS. 22 and 23.

FIG. 25 is partially a block diagram and partially a schematic partial longitudinal cross-sectional view, on an enlarged scale, of yet a further thrombectomy device.

FIG. 26 is a schematic transverse cross-sectional view taken along line XXVI—XXVI in FIG. 25.

FIG. 27 is a schematic partial longitudinal cross-sectional view, on an enlarged scale, of a thrombectomy device.

FIG. 28 is partially a block diagram and partially a schematic partial longitudinal cross-sectional view, on an enlarged scale, of another thrombectomy device.

FIG. 29 is a schematic transverse cross-sectional view taken along line XXIX—XXIX in FIG. 28.

FIG. 30 is a schematic transverse cross-sectional view taken along line XXX—XXX in FIG. 28.

FIG. 31 is a partial cross-section view of a cutting element and wire shown in FIGS. 28 and 29.

FIGS. 32 and 33 are diagrams depicting different steps in the use of the thrombectomy device of FIGS. 28–31.

DESCRIPTION OF THE PREFERRED EMBODIMENTS

Figure 9:
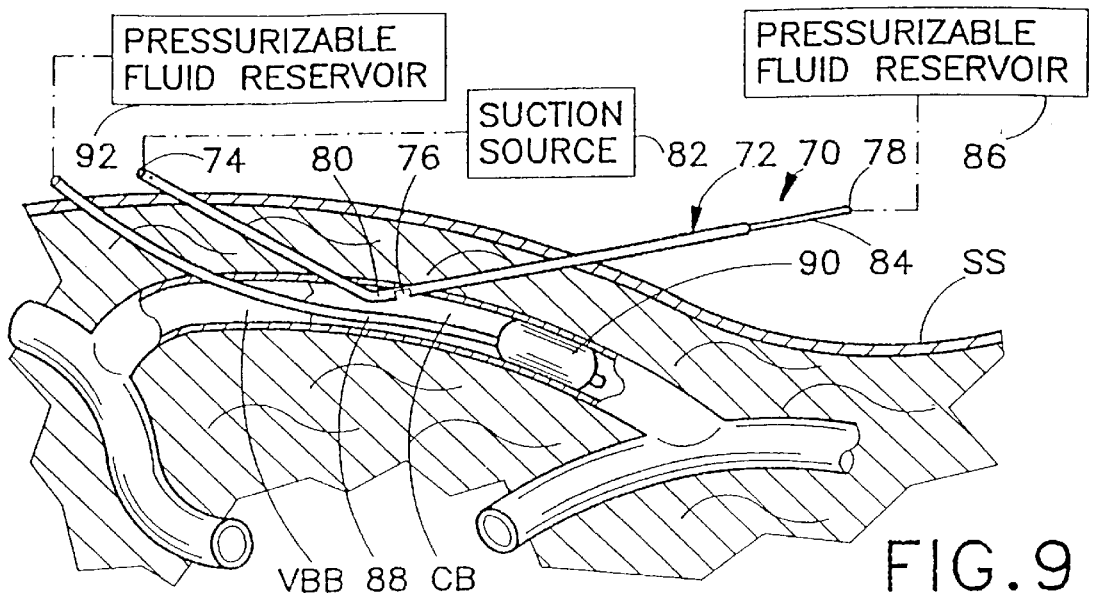
FIG. 9 is partially a schematic cross-sectional view of subcutaneous tissues and a vascular bypass and partially a schematic side elevational view of a device similar to that of FIG. 1, showing a modified clot removal technique.

As illustrated in FIG. 1, a minimally invasive surgical instrument or device 10 for removing a blood clot from a patient comprises an elongate tubular member 12 having a most distal first port 14, an intermediately located second port 16 and a most proximal third port 18 all spaced from each other along the tubular member. Tubular member 12 is provided with a bend or elbow 20 for facilitating the insertion of the distal end portion of the instrument into a patient so that distal port 14 and proximal port 18 both lie outside the patient, while intermediate port 16 lies inside a subcutaneous blood vessel, graft or vascular bypass VBP (FIG. 4).

A vacuum generator or suction source 22 is operatively connected to distal port 14 for applying suction to tubular member 12. A hollow obturator or drive rod 24 is shiftably inserted inside tubular member 12. At a proximal end, obturator 24 is operatively connected to an automatic reciprocating linear or translatory drive 26, while at a distal end the obturator 24 is provided with a circular blade or cutting edge 28 (FIG. 2). Drive 26 reciprocates obturator 24 back and forth across intermediate port 16. Upon a retraction stroke, intermediate port 16 is uncovered by obturator 24 to permit suction from suction source 22 to draw a blood clot BC in bypass VBP partially into the tubular member 12 through intermediate port 16 (see FIG. 4). A subsequent distally directed stroke of obturator 24 pushes cutting edge 28 against blood clot BC, thereby severing or macerating a portion thereof.

As further illustrated in FIG. 1, a supply or reservoir 30 is operatively connected via a luer lock or similar function adapter 32 to proximal port 18 for feeding a saline irrigation fluid to tubular member 12 upon a severing of a portion of blood clot BC by cutting edge 28 of obturator 24. The forward pushing motion of obturator 24 serves in part to assist the pulling action of suction source 22 to remove the severed clot portion from tubular member 12. A greater push is provided, however, by the saline irrigant from supply or reservoir 30. The irrigant is placed under pressure to facilitate the removal of severed clot portions from tubular member 12.

Obturator 24 is provided with an aperture 34 spaced from cutting edge 28 by approximately the same distance as that between intermediate port 16 and proximal port 18. Thus, upon a severing of blood clot BC during a distally directed stroke of obturator 24, obturator 24 is connected to pressurized irrigant reservoir 30 via proximal port 18 and aperture 34, thereby providing a timely flow of irrigant to force the severed clot material from tubular member 12. This pushing action is believed to so facilitate the removal of severed clot material that obturator 24 and tubular member 12 can be constructed with diameters thinner than those which might have only suction forces to remove severed clot material. Accordingly, small diameter tubes may be used to remove clots of relatively high viscosity.

Aperture 34 and proximal port 18 cofunction as a valve to permit the flow of irrigant only upon a severing of a blood clot BC by cutting edge 28 of obturator 24. During the pressurization of obturator 24 by the irrigant from reservoir 30, obturator 24 is juxtaposed to intermediate port 16 so as to prevent the flow of pressurizing fluid into bypass VBP.

This juxtaposition occurs periodically inasmuch as the invention contemplates an alternating cycle: initially a vacuum and other assist devices suck clots into the tubular clot-removal device. Only after that has been accomplished and the obturator changes position does the pressure cycle commence during which the obturator and/or pressurized saline solution ejects the clot material.

As shown in FIG. 2, cutting edge 28 is a circular edge provided by beveling obturator 24 at a distal end thereof.

As shown in FIG. 3, an obturator or drive rod element 36 insertable inside tubular member 12 is provided at a distal end with a longitudinally extending slot 38 formed along longitudinal edges with blades 40 and 42 for alternately slicing off portions of a blood clot sucked into tubular member 12 through intermediate port 16 by operation of suction source 22. Obturator element 36 is operatively connected at a proximal end to a reciprocating rotary drive 44. Drive 44 functions to shift blades 40 and 42 alternately past intermediate port 16.

It is to be noted that rotary drive 44 may be sufficient to macerate a clot to a particle size suitable for evacuation through tubular member 12 by suction. However, obturator element 36 may be additionally connected to a reciprocating drive for facilitating clot particle ejection or removal. Pressurized saline may or may not be provided. The requirements will vary depending on the characteristics of the particular clots.

As depicted in FIG. 4, a distal end of tubular member 12 is inserted through a skin surface SS of a patient into a subcutaneous tubular vascular component in the form of bypass VBP and subsequently out of bypass VBP and skin surface SS so that distal port 14 and proximal port 18 are located outside the patient while intermediate port 16 is located in bypass VBP. Upon completed insertion of the device, suction source 22 is operated to apply suction to distal port 14 to thereby draw blood clot BC in bypass VBP towards intermediate port 16. Upon a drawing of the clot at least partially into tubular member 12 through intermediate port 16, a portion of the clot is severed inside tubular member 12 by a distally directed stroke of obturator 24 or an angular shifting of obturator element 36. Subsequently, the severed clot portion is removed from tubular member 12 through distal port 14, in part because of the feeding of irrigant under pressure from reservoir 30 and in part because of the suction applied by source 22.

It is to be noted that the invention is used in conjunction with conventional mechanical surgical techniques for drawing clot material from opposite ends of bypass VBP towards intermediate port 16. For example, a wire (not illustrated) inserted through the same or a different puncture site may be manipulated to catch clotted clumps of blood and drag the captured clumps towards intermediate port 16 where the clumps are subjected to a suction force tending to draw the clot material into intermediate port 16. Also, Fogarty balloon catheters (not illustrated) may be used to push the clots, or another catheter (not illustrated) may inject fluid under pressure into the bypass graft to enhance further the flow of the clot to intermediate port 16 and out through tubular member 12.

FIGS. 5–7 illustrate respective alternative embodiments of the distal end of tubular member 12. As shown in FIG. 5, a sharp point 46 for skin penetration is provided by beveling the entire distal end of tubular member 12. Alternatively, as depicted in FIG. 6, the distal most port 14 in tubular member 14 is spaced from a sharpened distal tip 48 of the tubular member. As illustrated in FIG. 7, a tapered or sharpened distal tip 50 of tubular member 12 may be severed or otherwise separated from the rest of the tubular member, thereby forming port 14.

As shown in FIG. 8, an obturator or drive rod 52 extending through a vascular access tube 64 as described hereinabove may have a substantially solid distal end portion 54. That end portion 54 is formed with a groove 56 and a passageway 58 for enabling the transmission of irrigant from a proximal most port 68 in a distal direction upon the completion of a cutting stroke of obturator 52 at an intermediate port 66. Alternatively, a solid, but loosely fitting, obturator may be used, where pressurized irrigant flows around the obturator.

FIG. 9 illustrates a stage in a thrombectomy procedure utilizing a clot removal instrument or device 70. As described hereinabove with reference to FIG. 1, device 70 comprises an elongate tubular member 72 having a most distal first port 74, an intermediately located second port 76 (suction intake port) and a most proximal third port 78 all spaced from each other along the tubular member. Tubular member 72 is provided with a bend or elbow 80 for facilitating the insertion of the distal end portion of the instrument into a patient so that distal port 74 and proximal port 78 both lie outside the patient, while intermediate port 76 lies inside a subcutaneous blood vessel, graft or vascular bypass VBB.

A vacuum generator or suction source 82 is operatively connected to distal port 74 for applying suction to tubular member 72. A hollow obturator 84 is shiftably inserted inside tubular member 72. At a proximal end, obturator 84 is operatively connected to a pressurizable fluid reservoir 86 such as a syringe, while at a distal end the obturator 84 is provided with a cutting edge or blade (not shown in FIG. 9). Obturator 84 is manually reciprocated inside tubular member 72. Upon a distally directed cutting stroke of obturator 84, a portion of a blood clot CB sucked into tubular member 72 through port 76 is severed. In addition, cutting element or obturator 84 blocks port 76, thereby enabling or facilitating the forcible ejection of the severed blood clot mass from port 74 by the application of fluid pressure to tubular member 72 upon a pressurization of fluid reservoir 86. Upon a subsequent retraction stroke of cutting element or obturator 84, clot intake port 76 is uncovered by obturator 84 to permit suction from suction source 82 to draw another portion of blood clot CB in bypass VBB partially into the tubular member 72 through intermediate port 76. A subsequent distally directed stroke of obturator 84 pushes the cutting edge thereof against blood clot CB, thereby severing or macerating a portion thereof. Again, as described hereinabove with respect to FIG. 1, saline irrigant from reservoir 86 provides sufficient pressure to remove any severed clot mass which would otherwise become stuck inside tubular member 72.

As further illustrated in FIG. 9, a catheter 88 with a collapsed balloon 90 attached to an external surface may be inserted into the patient's vascular system, particularly into bypass VBB, so that the balloon is located on a distant side of the blood clot CB. A fluid reservoir 92 (e.g., syringe) is then pressurized to inflate balloon 90, as shown in FIG. 9. Subsequently, a traction force is placed on catheter 88 to drag blood clot CB along bypass VBB towards clot intake port 76 of instrument 70. This procedure facilitates removal particularly of a large clot CB.

Figure 10B:
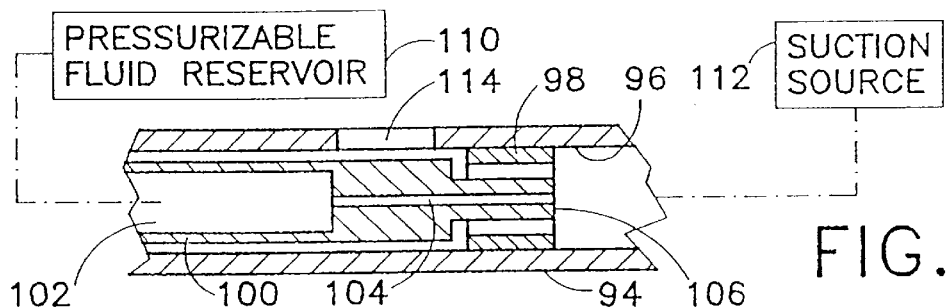
FIG. 10B is a view similar to FIG. 10A, showing the device of FIG. 10A in a cutting or macerating phase of an operating cycle.
Figure 10A:
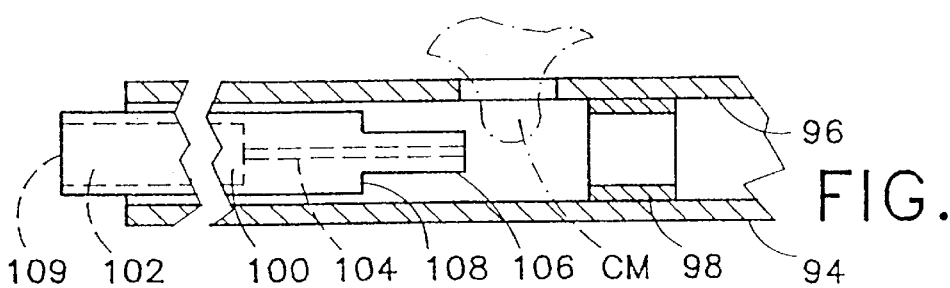
FIG. 10A is partially a block diagram and partially a schematic partial longitudinal cross-sectional view, on an enlarged scale, of a modified thrombectomy device, showing the device in a clot intake phase of an operating cycle.

As depicted in FIGS. 10A and 10B, a modified thrombectomy device comprises a tubular member 94 provided on an inner surface 96 with a sleeve 98. A cutting element 100 in the form of an obturator has a longitudinally extending channel 102 with a narrowed distal end segment 104. The distal end of cutting element or obturator 100 is provided with an axially extending projection 106 which is insertable into sleeve 98 upon a distally directed cutting stroke of cutting element or obturator 100, as shown in FIG. 10B. Projection 106 partially defines a shoulder 108 which is engageable with sleeve 98. Channel 102 of cutting element or obturator 100 communicates at a proximal port 109 (FIG. 10A) with a pressurizable fluid reservoir 110 (FIG. 10B), while an end of tubular member 94 opposite cutting element 100 communicates with a suction source or vacuum generator 112.

Upon a drawing of a clot mass CM into tubular member 94 through a window or clot intake port 114 therein, a distally directed stroke of cutting element 100 severs the clot mass. The clot mass is forced by projection 106 through sleeve 98, thereby macerating or reducing the severed clot mass in size. This maceration or reduction in size further facilitates the removal of the severed clot mass from tubular member 94. The severed clot mass is also crushed (partially) between sleeve 98 and shoulder 108. In addition, the severed clot mass is subjected to a jet of saline irrigant (not shown) exiting cutting element 100 via narrowed distal end segment 104 of channel 102.

Figure 11:
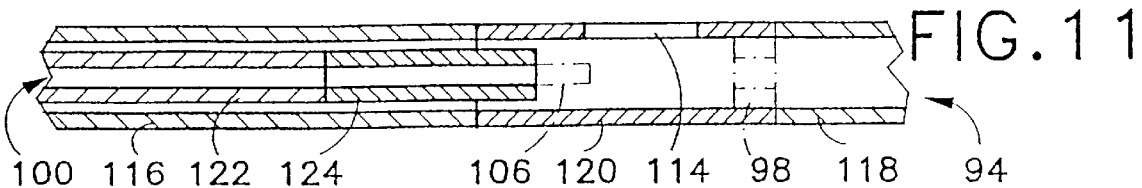
FIG. 11 is a schematic partial longitudinal cross-sectional view, on an enlarged scale, of a thrombectomy device similar to that of FIGS. 10A and 10B, showing particular implementations with respect to materials.

As illustrated in FIG. 11, tubular member 94 may be partially made of a flexible material. More particularly, tubular member 94 may include a flexible proximal section 116 connected to a flexible distal section 118 by a rigid section 120 which includes window or clot intake port 114. In this case, cutting element 100 has a flexible body 122 and a rigid tip 124. If sleeve 98 and projection 106 are not omitted, they are preferably provided on rigid section 120 and rigid tip 124, respectively.

The modified thrombectomy device of FIG. 11 is particularly useful in removing clots from blood vessels which do not lie near a skin surface. Rigid section 120 may be positioned proximally to an intravascular clot via well known guidewire techniques.

As depicted in FIGS. 12A, 12B, and 12C, another thrombectomy device comprises a tubular member 126 provided with a cross-sectionally D-shaped cutting element or obturator 128 which defines a suction channel 130 and a pressurization channel 132. Suction channel 130 is connected to a suction source or vacuum generator 134, while pressurization channel 132 is coupled at an irrigant inlet port 135 to a pressurizable irrigant or saline reservoir 136. At a distal end cutting element 128 is beveled to define a cutting edge or blade 138. Upon a distally directed stroke of cutting element 128 (compare FIGS. 12A and 12B), cutting edge 138 moves past a clot intake window or port 140 in tubular member 126 to sever a potion of clot projecting into the tubular member through window 140. In the event that the suction from source 134 is insufficient to pull the severed clot portion from tubular member 126, the pressure of fluid in reservoir 136 is increased. Cutting element remains in the position shown in FIG. 12B to thereby close or block window 140 and enable or facilitate a build-up of fluid pressure behind the severed clot mass sufficient to forcibly eject the clot mass from tubular member 126. As indicated by an arrow 142 in FIG. 12B, saline irrigant from reservoir 136 flows through irrigation channel 132 and around the beveled leading edge of cutting element 128 into suction channel 130.

Figure 14:
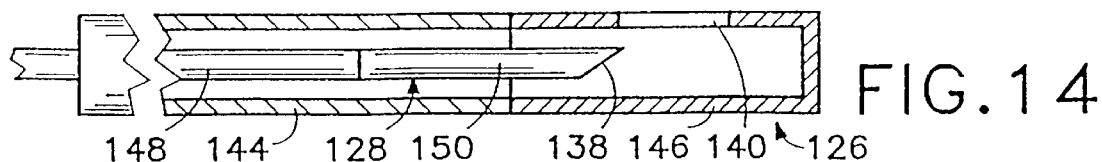
FIG. 14 is a schematic partial longitudinal cross-sectional view, on an enlarged scale, of a thrombectomy device similar to that of FIGS. 12A, 12B and 13, showing particular implementations with respect to materials.

As illustrated in FIG. 14, the thrombectomy device of FIGS. 12A, 12B and 13 may be partially flexible for insertion through arcuate blood vessels. More specifically, tubular member 126 may have a flexible body segment 144 and a rigid tip 146 provided with window 140. Similarly, cutting element or obturator 128 may have a flexible body segment 148 and a rigid tip 150 provided with cutting edge 138.

It is to be noted that in the thrombectomy probe embodiments of FIGS. 12A, 12B, 13 and 14, as well as in all of the other thrombectomy devices disclosed herein, the cutting element 128 has a cutting edge or blade 138 functioning to sever a clot mass pulled into tubular member 126 through intake port or window 140 and also has a surface (internal or external) which functions to close the window during a subsequent pressurization of the tubular member to eject a stuck clot therefrom. Although not every severed clot mass will require forcible ejection via hydrostatic pressurization or hydrodynamic forces, every thrombectomy procedure utilizing a thin tubular member as disclosed herein will require one or more applications of fluid pressure to hydrostatically or hydrodynamically eject a lodged clot mass from the tubular member.

As depicted in FIG. 15, another thrombectomy device comprises a tubular member 152 having a narrow section 154 connected at an irrigant inlet port 156 to a pressurizable reservoir 158 containing a saline solution or irrigant. Tubular member 152 has a wide section 160 in which a cutting element 162 in the form of an obturator is slidably disposed for motion past a clot intake window or port 164. Cutting element 162 is hollow, i.e., defines a fluid flow channel 166 which communicates with a suction source or vacuum generator 168. Cutting element 162 enters tubular member 152 at an opening (not shown) therein. FIG. 16 shows the thrombectomy device of FIG. 15 provided with a bend 170 in narrow section 154 proximate to wide section 160.

As indicated in FIG. 17, the thrombectomy device of FIG. 15 (or 16) is used by inserting narrow section 154 into a vascular component VC, as indicated by arrow 172, so that window 164 is disposed inside vascular component VC and so that the opposite ends of tubular member 152, as well as the irrigant inlet and suction ports thereof) are disposed outside the patient. Pressurizable irrigant is fed into tubular member 152 via narrow section 154, as indicated by an arrow 174, while macerated clot mass is removed via wide section 160 (arrow 176).

It is to be noted that irrigant from any pressurizable reservoir (e.g., syringe) disclosed herein may flow or leak at a low rate for lubrication purposes during unclogged operation of the respective thrombectomy device. When a severed clot mass becomes stuck in the tubular member, the pressure of the fluid irrigant is increased to impose an ejection force on the stuck clot mass.

In FIG. 18, a tubular member 178 of a thrombectomy device has a narrow irrigant inlet section 180 and a wide suction section 182. A cutter element 184 comprises a cylindrical segment perforated with a multiplicity of bores 186 so that the cutter element is moved in a cutting stroke, as indicated by an arrow 188, upon the application of fluid pressure to a conical rear surface 190 of the cutting element via narrow irrigant inlet section 180. After a severing of a clot mass (not shown) protruding into tubular member 178 via an opening, port or window 192 and after removal of the severed clot mass from the tubular member, a cable or wire 194 attached to cutter element 190 is pulled to return the cutting element to a precutting position in which window 192 is open for drawing in further clot mass.

In the embodiment of FIG. 18, as in essentially all the thrombectomy devices discussed herein, fluid pressure is used to eject any severed clot mass which becomes lodged in the tubular member. The cutting element is maintained in position over the clot intake window or port 192 to ensure the generation of sufficient pressure to eject the ledged clot material. In the embodiment of FIG. 18, a sleeve (not shown) may be provided in tubular member 178 downstream of window 192 to arrest downstream motion of cutting element 184 upon closure of window 192 thereby. Alternatively, wire 194 may be used to hold cutting element 184 in position during a clot ejection phase of a thrombectomy procedure. In any event, bores 186 are sufficiently small in total cross-sectional area to enable fluid pressure to push cutting element 184 past window 192, but sufficiently large in total cross-sectional area to enable pressurization of the tubular member for ejecting a stuck clot mass.

FIGS. 19 and 20 show a slight modification of the thrombectomy device of FIG. 18, in which a tubular member 196 has an essentially uniform diameter or cross-section and in which a rear surface 198 of a cylindrical cutting element 200 is planar rather than conical. A pressurizable fluid reservoir 202 is connected to tubular member 196 at an end opening or port (not shown) thereof. Otherwise, the essential structure and operation of the thrombectomy device of FIGS. 19 and 20 is the same as that of the thrombectomy device of FIG. 18, as indicated by the use of like reference designations.

FIG. 21 shows a generalized thrombectomy device with a tubular member 204, a clot intake port 206, and an irrigant port 208 at one end. In addition, an inflatable balloon 210 is provided on tubular member 204 for occluding a clotted vascular component and dragging a clot to a desired location in the vascular component for removal. It is to be understood that balloon 210 may be provided on any of the thrombectomy devices disclosed herein which are longitudinally shiftable along a clotted vascular component during a thrombectomy procedure. As additionally shown in FIG. 21, a first pressurizable fluid reservoir 212 is connected to a cutting obturator 214 slidably disposed inside tubular member 204. Pressurizable fluid reservoir 212 supplies a fluid to the tubular member for purposes of lubricating the sliding relationship between obturator 214 and tubular member 204 and for purposes of forcibly ejecting a stuck clot mass from tubular member 204. Another pressurizable fluid reservoir 214 communicates with balloon 210 via tubular member 204 for inflating the balloon as indicated at 216.

As illustrated in FIGS. 22 and 23, a spring loaded thrombectomy device comprises a tubular member 218 provided with a longitudinally extending partition 220 dividing the lumen of tubular member 218 into a fluid feed channel 222 and a suction channel 224. A pressurizable fluid reservoir 226 communicates with fluid feed channel 218, while a suction source or vacuum generator 228 communicates with suction channel 224, both at an opening or port (not shown) at a proximal end of tubular member 218. A cutting element 230 is slidably disposed in suction channel 224 at a distal end thereof and is biased in the distal direction by a helical compression spring 232 disposed between the cutting element and a sleeve 234 attached to partition 220 and to tubular member 218 along an inner surface thereof. A wire 236 extends through cutting element 230 and along suction channel 224 for pulling the cutting element in a proximal direction in opposition to a force exerted by spring 232, thereby moving cutting element 230 past a clot intake window or port 238 to sever an inwardly protruding clot mass and to close the window for enabling or facilitating a pressurized ejection of the severed clot mass. A ball 240 on wire 236 transmits force between wire 236 and cutting element 230. Cutting element 230 is provided with longitudinally extending bores 242 for delivering pressure fluid from a distal end of fluid feed channel 218 to suction channel 224 upstream of a stuck clot mass.

Fluid from reservoir 226 flows along a path extending through feed channel 218, through bores 242 in cutting element 230 and past window or port 238 into suction channel 224. In virtually all of the thrombectomy devices disclosed herein, pressure fluid flows such a path. Fluid pressure upstream of a clogging clot mass is augmented by the closing of the clot intake port by the cutting element.

FIG. 24 depicts a variation of the thrombectomy of FIGS. 22 and 23, in which helical compression spring 232 is replaced by a plurality of smaller compression springs 244 angularly spaced from one another about an inner surface of tubular member 218. Those skilled in the art can readily appreciate that other variations in the structure for reciprocating the cutting element may be derived. For example, instead of compression springs, tension springs might be used.

FIGS. 25 and 26 illustrate a thrombectomy device wherein reciprocation of a cutting element 246 is accomplished hydraulically. A saline fluid from a periodically pressurizable reservoir 248 is fed to an opening or port (not shown) at a proximal end of a fluid feed channel 250 defined in a tubular member 252 by a partition 254. Cutting element 246 has an elongate eccentrically located drive member 256 located along an inner surface of tubular member 252 and projecting into channel 250 at a distal end thereof, the drive member 256 having a pressure face 258 acted on by the fluid in channel 250. Upon a pressurization of channel 250, cutting element 246 moves in a distal direction, thereby uncovering a clot intake port 260 in tubular member 252. Fluid from channel 250 leaks though bores 262 provided in finger 256 to a chamber 264 at a distal end of tubular member 252. Pressure in that chamber can be increased sharply to force cutting element 246 in the proximal direction, thereby severing any clot mass sucked into tubular member 252 through port 260 owing to a depressurization of a suction channel 266 by a suction source or vacuum generator 268. Cutting element 246 has a pressure face 270 which is greater in surface area than finger pressure face 258, whereby a force may be exerted on cutting element 246 to produce a cutting stroke. Pressure is reduced to enable a distally directed return stroke. Cutting element 246 is provided with additional bores to enable forcible clot mass ejection, as described above.

FIG. 27 illustrates, in generalized format, a thrombectomy device wherein a cutting element 272 is slidably disposed outside a tubular thrombectomy member 274 for motion past a clot intake port 276 to sever a clot mass (not shown) sucked into the tubular member through the port 276 and to temporarily cover the window during extraction of the clot at least by a suction force applied to one end of the instrument, as schematically indicated by an arrow 278. An irrigating or lubricating fluid is fed to tubular member 274, for example, from an opposite end thereof, as indicated by an arrow 280. In the event that the suction force is inadequate to extract the severed clot mass, the irrigant may be pressurized, e.g., by a syringe or other pressurizable fluid source 282, to forcibly eject the clot mass. The closing of port 276 by an inner surface of cutting element 272 enables or at least facilitates the generation of sufficient pressure to eject the severed clot mass.

It is to be noted that an external cutting element, as described with reference to FIG. 27, may be utilized in a thrombectomy device wherein pressure fluid is fed to the tubular member at the same end thereof to which a suction source is coupled. In that event, a partition divides the tubular member into a fluid feed channel and a suction channel. It is to be further noted that the pressure fluid flows along a path past the clot intake opening or port and through the cutting element. This is the case even where the cutting element extends from the irrigant inlet end (left side in FIG. 27).

In another embodiment of a thrombectomy device illustrated in FIGS. 28–31, reciprocating movement of a cutting element 284 is implemented via a stiff wire 286 which is connected to the cutting element, as described below. Wire 286 extends eccentrically along a fluid feed channel 288 defined by a partition wall 290 located along an inner surface of a tubular thrombectomy member 292. Partition wall 290 projects at a distal end 294 into a D-shaped channel 296 (FIG. 29) in cutting element 284.

As shown in FIGS. 29 and 31, wire 286 traverses a bore 298 (FIGS. 29 and 31) in a wall 300 (FIG. 29) of cutting element 284. Wire 286 is provided with an external screw thread 302 which threadingly mates with an internal screw thread 304 in bore 298. At a distal side of cutting element 284, wire 286 extends through an aperture 306 in tubular member 292.

During a thrombectomy operation, a clot mass is sucked into tubular member 292 through an opening or port 308 therein, through the operation of a suction source 310 connected to a proximal end of a suction channel 312 defined in tubular member 292 by partition wall 290. Wire 286 is then pushed in a distal direction to move cutting element 284 and particularly a cutting edge 314 thereof past opening or port 308. At least a portion of the severed clot mass is disposed inside channel 296 of cutting element 284. A suction force applied by suction source 310 via channel 312 pulls the severed clot mass through channel 296 in cutting element 284 and proximally through channel 312. In the event that the severed clot mass becomes lodged inside cutting element 284 or suction channel 312, a fluid reservoir 316 communicating with fluid feed channel 288 via an opening or port 318 is pressurized to build up a back pressure to forcibly eject the lodged clot mass from tubular member 292. Subsequently to the extraction of the severed clot mass from tubular member 292, wire 286 is pulled to move cutting element 284 back in the proximal direction to uncover opening 318 and thereby initiate another cutting cycle.

As depicted diagrammatically in FIGS. 32, the thrombectomy device of FIGS. 28–31 may be used in a procedure wherein a guidewire 320 is first inserted into a tubular vascular component TVC of a patient. Subsequently to the placement of guidewire 320, tubular member 292 with cutting element 284 is inserted into vascular component TVC over guidewire 320, as shown in FIG. 32. Then guidewire 320 is withdrawn from the patient and replaced with wire 286, as indicated in FIG. 33. Wire 286 is a kind of guidewire. The insertion of wire 286 through aperture 306 is facilitated by a curved inner surface 322 of tubular member 292 at the distal end thereof (FIG. 28).

Figure 34:
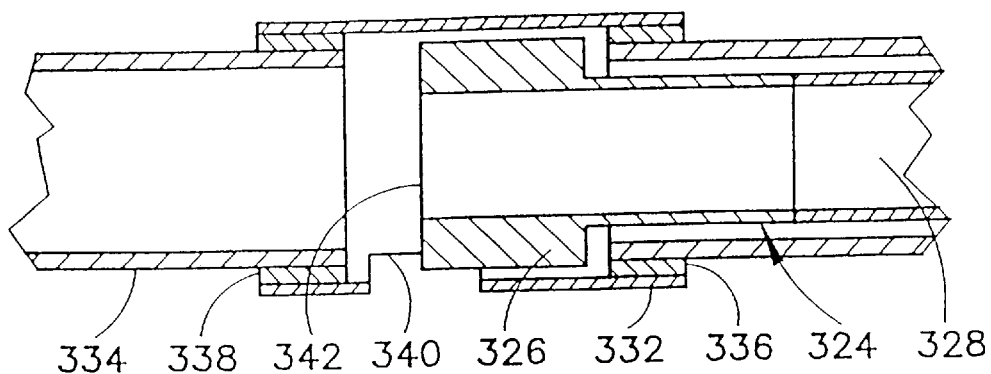
FIG. 34 is a schematic partial longitudinal cross-section view of a thrombectomy device, illustrating a manufacturing technique.

FIG. 34 is provided to depict a manufacturing process for a partially flexible thrombectomy device as described herein. The process is, however, also applicable to completely rigid thrombectomy devices. A cutting element 324 including a rigid distal tip 326 and a flexible body 328 is inserted through a flexible outer tube 330. A rigid sleeve 332 is then attached to an outer surface of tube 330 and to another flexible tube 334 via annular welds or coupling elements 336 and 338. Sleeve 332 has a clot intake opening or port 340, while tip 326 of cutting element 324 is provided with a cutting edge 342.

Figure 35:
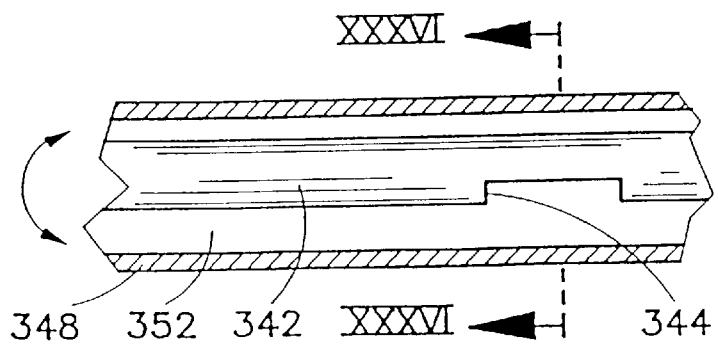
FIG. 35 is a schematic partial longitudinal cross-sectional view, on an enlarged scale, of yet another thrombectomy device.
Figure 36:
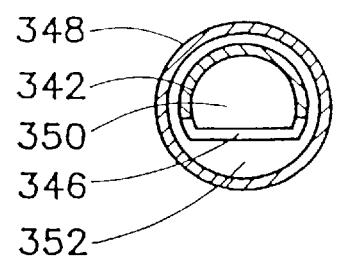
FIG. 36 is a transverse cross-sectional view taken along line XXXVI—XXXVI in FIG. 35.

FIGS. 35 and 36 depict a thrombectomy device with a cross-sectionally D-shaped cutter element 342 provided with a cutting window 344. A wall 346 of cutter element 342 divides a lumen (not designated) of a tubular member 348 into a suction channel 350 and an irrigation or positive pressurization channel 352. The cutter of FIGS. 35 and 36 may be reciprocated, or alternatively, rotated. In a rotating mode of operation, cutter element 342 remains longitudinally fixed relative to tubular member 348. As window 344 becomes aligned with an intake port (not shown) in tubular member 348, a negative pressure in suction channel 350 draws a clot or other organic material into the tubular member through the intake port. Further rotation of cutter element 342 closes the intake port and simultaneously cuts off a portion of the clot or other material for subsequent removal or ejection via the tubular member.

Figure 37:
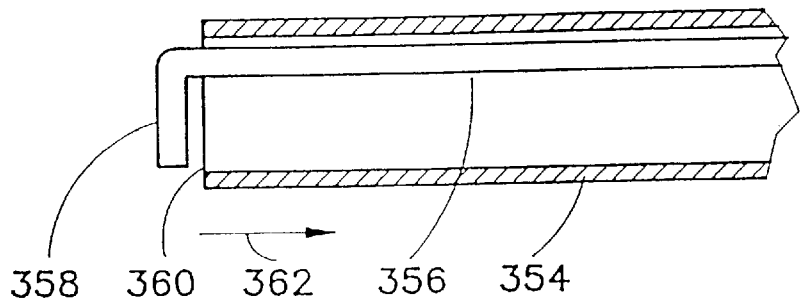
FIG. 37 is a schematic partial longitudinal cross-sectional view, on an enlarged scale, of yet a further thrombectomy device.

As illustrated in FIG. 37, a thrombectomy device may include a tubular member 354 through which an eccentrically disposed hollow irrigation tube or drive rod 356 slidably extends. At a distal end, irrigation tube or drive rod 356 is provided with a cutter element in the form of a cap 358 which closes off a clot-intake port or opening 360 upon a shifting of the irrigation tube in the proximal direction, as indicated by an arrow 362. Upon the closure of intake port 360 by cap 358, irrigation fluid is introduced from drive rod 356 through an irrigation outlet on a proximal side of cap 358 into tubular member 354 to provide a pressure differential or gradient across severed clot material to facilitate ejection of any stuck clot material. Irrigation tube or drive rod 356 is located along an inner surface of tubular member 354, thereby maximizing the amount of clot material which may be severed and transported along tubular member 354 to a proximal end thereof.

Furthermore, as compared to other clot disruption devices, this device only processes clot after the clot has been moved internal to the device via the associated suction capabilities. Only then is a portion of the clot severed and ejected, without any possibility of loss into the patient's vascular system. The remaining clot in the vascular vessel as yet unprocessed is not affected in any way by the device.

A clot removal device in accordance with the invention entails a self-limiting anti-clogging system that inherently slows or stops the intake procedure concurrently with any clot buildup in the suction section of the clot ejection path of the tubular member. This anti-clogging feature does not interfere with the ongoing fluid pressure cleaning and ejecting system.

Figure 38:
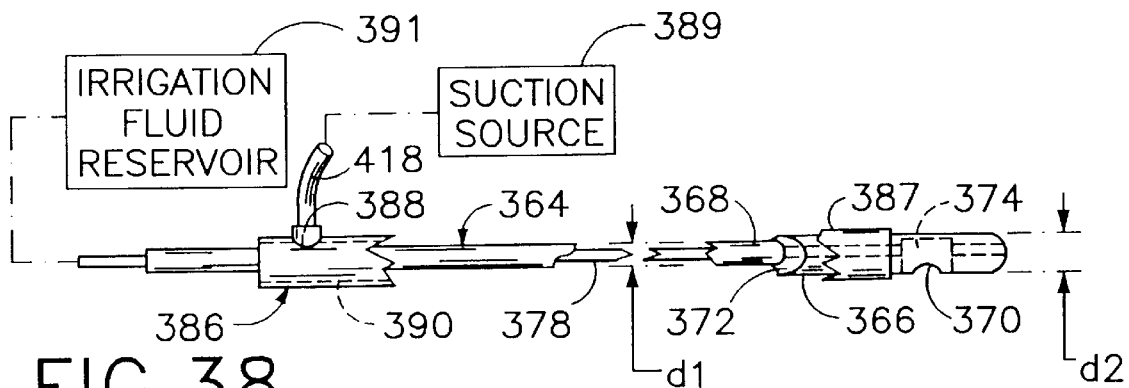
FIG. 38 is a schematic side elevational view, partially broken away and on an enlarged scale, of a thrombectomy device or assembly in accordance with the present invention.

As illustrated in FIG. 38, a minimally invasive thrombectomy device comprises a tubular member 364 having a distal end portion 366 and a proximal portion 368. Proximal portion 368 has a maximum outer transverse dimension or diameter smaller d1 which is smaller than a maximum outer transverse dimension or diameter d2 of distal end portion 366. Distal end portion 366 of tubular member 364 is provided with a clot-intake port 370, and tubular member 364 is further provided with a clot outlet port 372 disposed proximally of clot-intake port 370 and distally of proximal portion 368 of tubular member 364. A cutter element 374 provided with a cutting edge 376 on a proximal side is movably disposed in tubular member 364.

Figure 39:
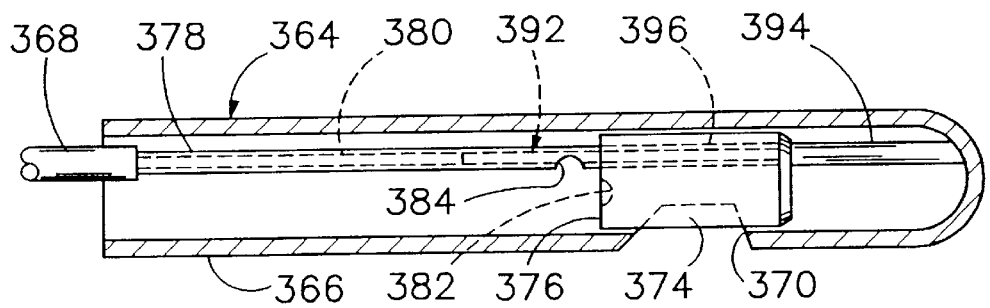
FIG. 39 is a schematic side elevational view, on an even larger scale, of a portion of the thrombectomy device illustrated in FIG. 38.

As further illustrated in FIG. 38, a drive rod 378 extends through proximal portion 368 of tubular member 364 and into distal end portion 366 and is connected at a distal end to cutter element 374 for moving cutting edge 376 past clot-intake port 370. Drive rod 378 has a longitudinally extending lumen 380 (FIG. 39). Either cutter element 374 or a distal end of drive rod 378 is provided with an irrigation outlet 382 or 384 which communicates with lumen 380.

The thrombectomy device or assembly of FIG. 38 further comprises a catheter 386 which has a proximal end provided with a suction port 388 communicating with a lumen 390 of catheter 386. Tubular member 364 traverses catheter lumen 390 so that clot-intake port 370 is disposed outside catheter 386 and clot outlet port 372 is disposed inside the catheter. The maximum transverse dimension d1 of proximal portion 368 is substantially narrower than the lumen 390 of catheter 386, thereby markedly increasing instrument flexibility and facilitating passage of a severed clot mass through catheter 386 alongside proximal portion 368 of tubular member 364 to suction port 388 during a thrombectomy procedure.

In a minimally invasive thrombectomy method utilizing the device of FIG. 38, a distal end section of catheter 386 is inserted into a vascular component (e.g., bypass) of a patient. Subsequently, tubular member 364 is inserted into catheter 386 so that clot-intake port 370 is disposed outside a distal end portion 387 of catheter 386 and clot outlet port 372 is disposed inside catheter 386. Upon that disposition of tubular member 364 relative to catheter 386, drive rod 378 is shifted or translated in a distal direction so that cutter element 374 moves to open clot-intake port 370. Upon the opening of port 370, suction is applied to catheter 386 by a vacuum generator or suction source 389 via suction port 388 to pull clot material through clot-intake port 370 into distal end portion 366 of tubular member 364. Drive rod 378 is then pulled in the proximal direction to move cutting edge 376 past clot-intake port 370, thereby severing the clot material pulled into distal end portion 366. By a further application of suction force by suction source 389, the severed clot material is drawn in a proximal direction from distal end portion 366 of tubular member 364, through clot outlet port 372 and along catheter 386, outside of proximal portion 368 of tubular member 364, to the suction port of catheter 386. During this drawing of the severed clot material, an irrigation source 391 delivers fluid into tubular member 364 upstream of the clot material to facilitate the drawing of the severed clot material. The fluid serves to break the suction upstream of the clot, thereby ensuring that a pressure differential continuously exists across the severed clot mass.

Preferably, the irrigation fluid from source 391 is fed to tubular member 364 through lumen 380 of drive rod 378 to irrigation outlet 382 or 284. The irrigation outlet is thus placed in a most distal position, to ensure that the fluid feed always comes in upstream of a severed clot mass.

As further illustrated in FIG. 39, a valve 392 is disposed in tubular member 364 for closing irrigation outlet 384 during a clot suctioning phase of an operating cycle and for opening irrigation outlet 384 after a proximally directed clot-severing stroke of cutting edge 388 past clot-intake port 370. Specifically, valve 392 includes a longitudinally extending wire 394 connected to tubular member 364 at a distal end thereof, the wire extending into a channel 396 provided in cutter element 374. Channel 396 is colinear with lumen 380 of drive rod 378 so that wire 394 can extend into lumen 380 of drive rod 378 and cooperate with irrigation outlet 384 to effectuate the desired valving action. Thus, irrigation outlet 382 or 384 is automatically opened upon a shifting of drive rod 378 and, therefore, cutter element 374 in a proximal direction past a predetermined, fixed location relative to tubular member 364. Upon a shifting of drive cutter element 374 in a distal direction past the predetermined fixed location determined by the proximal end of wire 374, irrigation outlet 384 is closed, thereby preventing leakage of irrigation fluid out of the thrombectomy device into a surrounding vascular component via clot-intake port 370 and further preventing the weakening of the suction force for pulling in a clot mass.

Figure 40:
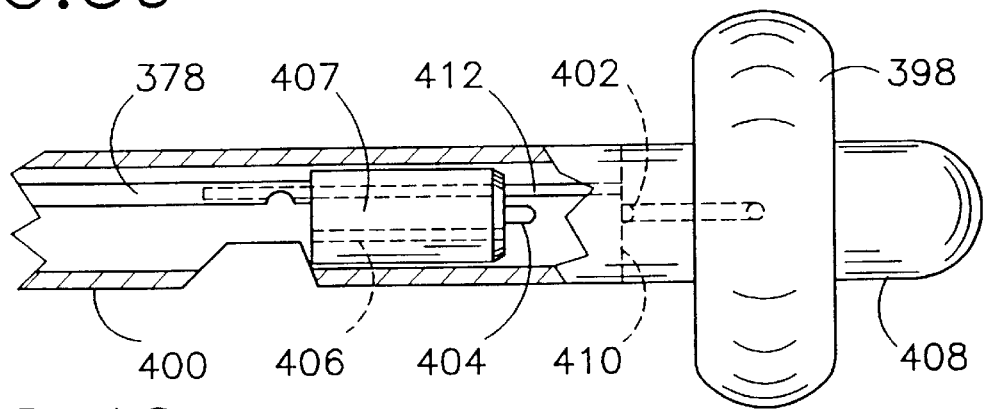
FIG. 40 is a schematic side elevational view showing a modification of the thrombectomy device illustrated in FIG. 39.

As depicted in FIG. 40, a balloon 398 may be attached to a tubular member 400 at a distal end thereof. A one-way valve 402 is provided at the distal end of tubular member 364 for preventing deflation of balloon 398 during use in a thrombectomy procedure. In addition, a valve opening projection 404 is provided on a distal end face of cutter element 374 for opening one-way valve 402 by pushing drive rod 378 and concomitantly cutter element 374 to a sufficiently distal position.

To inflate balloon 398, a pressurization fluid is fed to distal end portion 366 of tubular member 364 via drive rod lumen 380 and possibly also via suction port 388, catheter 386 and clot outlet port 372. During this pressurization of distal end portion 366 and the concomitant inflation of balloon 398, cutter element 374 is positioned over clot-intake port 370, thereby closing the port and ensuring that the fluid is directed to balloon 398 to inflate the balloon. (Alternatively, the entire device (except the balloon) may be withdrawn into the introducer sheath to close the clot-intake port.) The pressurization fluid moves through a duct 406 in a cutter element 407 and through one-way valve 402 into balloon 398. After inflation of balloon 398, tension is exerted on tubular member 364 to pull the balloon through the vascular component into which tubular member 364 has been previously inserted. The device is then used, as described above, to remove clot material which has been gathered by the shifting of balloon 398 through the vascular component. To deflate balloon 398 prior to removal of the instrument from the vascular system of a patient, cutter element 374 is shifted in the distal direction to push projection 404 into valve 402 to open the valve and deflate the balloon.

In the embodiment of FIG. 40, balloon 398 is attached to an extension 408 of tubular member 400 disposed distally of a transverse wall 410. A wire 412 substantially identical to wire 394 (FIG. 39) extends longitudinally in a proximal direction from wall 410 to form a valve as discussed above with reference to FIG. 39. The drive rod 378 (same as in FIGS. 38 and 39) may be spring loaded to bias it in a proximal direction so that projection 404 is maintained at a minimum distance from one-way valve 402 during clot-suction and removal operations.

Figure 41:
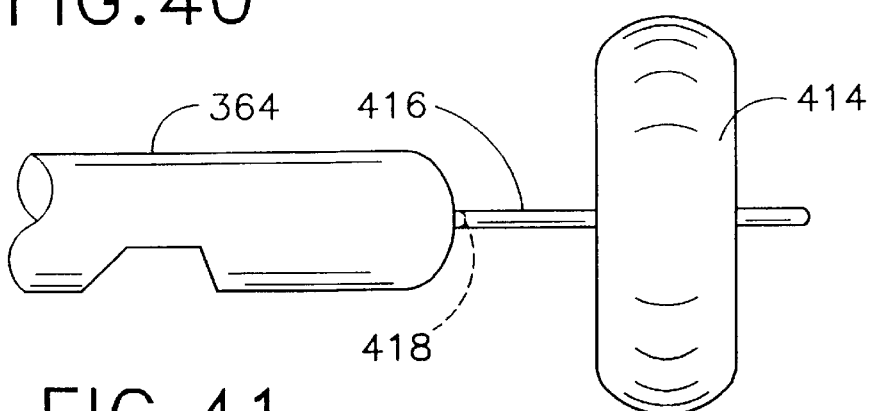
FIG. 41 is a schematic side elevational view showing another modification of the thrombectomy device illustrated in FIG. 39.

As illustrated in FIG. 41, a balloon or bladder 414 similar to balloon 398 may be attached to tubular member 364 via a tube 416 provided with a one-way valve 418 similar to valve 402. The remaining structure and operation of the device of FIG. 41 is substantially similar to the structure and operation of the device of FIG. 40.

Figure 42:
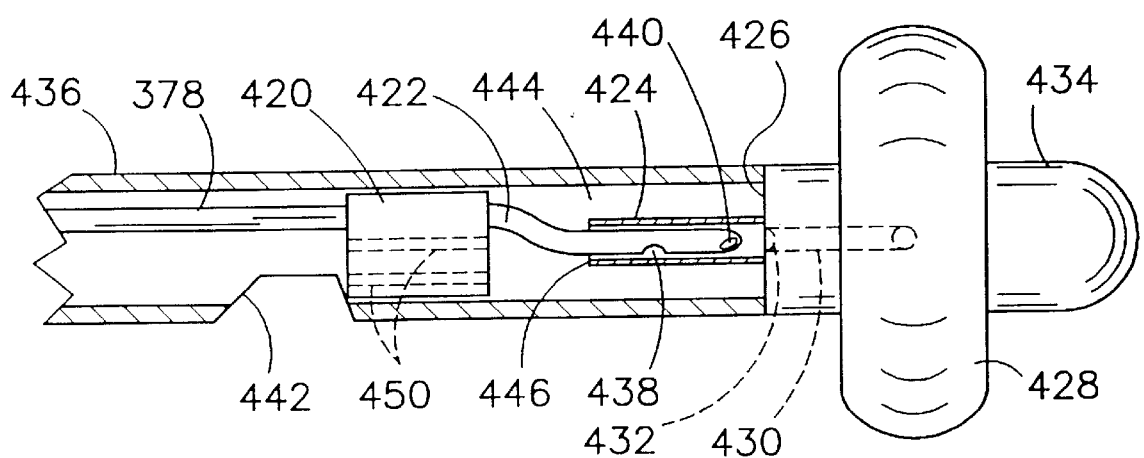
FIG. 42 is a schematic side elevational view showing yet another modification of the thrombectomy device illustrated in FIG. 39.

As depicted in FIG. 42, a cutter element 420 is provided on a distal side with a bent tube 422 which communicates with lumen 380 (not shown) of drive rod 378 and which extends into a valve-closure sleeve 424. Sleeve 424 is connected to a transverse wall or partition 426 and projects in a proximal direction towards cutter element 420. Sleeve 424 communicates with a balloon 428 (shown inflated) via a duct 430 and a one-way valve or self-sealing membrane 432. Balloon 428 is attached to an extension 434 of a tubular member 436 similar to tubular member 364 of FIG. 38.

Tube 422 is provided at a distal end with an irrigation port or outlet 438 and a balloon inflation opening 440. To inflate balloon 428 from a collapsed insertion configuration (not shown), drive rod 378 is pushed in the distal direction from a suction or clot-intake position shown in FIG. 42. A distal tip of tube 422 including opening 440 is pushed through one-way valve or self-sealing membrane 432 into duct 430. Then fluid pressure is applied via drive rod 378, tube 422, and duct 430.

After the inflation of balloon 428, drive rod 378 is retracted to the clot-intake position shown in FIG. 42. Suction is then applied to draw clot material into tubular member 436 through a clot-intake opening or port 442. Subsequently, drive rod 378 is drawn in the proximal direction to move cutter element 420 past clot-intake opening 442. Just after cutter element 420 completes a cutting stroke and closes off clot-intake opening 442, irrigation port 438 clear a proximal end 444 of closure sleeve 424, thereby enabling the feeding of pressurization fluid into a chamber 446 defined by tubular member 436, cutter element 420 and wall 426. While cutter element closes clot-intake opening 442, this fluid flows from chamber 446 through passageways 450 in cutter element 420 to an upstream side of the severed clot material. The fluid feed serves, together with the suction applied via port 388 (FIG. 38), to generate a pressure differential which moves the severed clot material along tubular member 436 and catheter 386 (FIG. 38) and out through suction port 388. After the completion of the cutting operation, drive rod 378 may be pushed back in the distal direction so that irrigation port 438 is covered by sleeve 424, thereby preventing the feeding of fluid into the vascular system of the patient. The device is now ready for another cycle of a thrombectomy.

After the thrombectomy has been completed, balloon 428 is deflated by moving drive rod 378 and accordingly tube 422 so that the distal tip thereof opens one-way valve or self-sealing membrane 432, thereby enabling the flow of fluid from balloon 428 through duct 430 and tube 422 to drive member 378. A suction source may be temporarily connected to drive rod 378 to expedite the extraction of fluid from balloon 428.

The embodiment of FIG. 42 is especially space efficient in that the same channel (lumen 380 of drive rod 378) is used both for balloon inflation and for irrigation and pressure differential generation.

A thrombectomy assembly as illustrated in FIGS. 38–42 is advantageous for several reasons. The cross-sectional area available for clot removal is enlarged because tubular member 364 has a reduced diameter for much of its length (i.e., along proximal portion 368). In addition, catheter 386 may be maintained in the patient and used for other purposes. Moreover, the suction is attached to catheter 386 rather than to tubular member 364, thereby facilitating insertion and removal of the tubular member. A suction tube 418 (FIG. 38) attached to port 388 may be provided with a valve (not shown) for turning off the suction when tubular member 364 is removed from catheter 386. Balloon 398, 414 or 428 is provided on the tubular member of the thrombectomy device and inflation occur via the channels (i.e., lumen 380 and/or lumen 390) provided for other purposes. This again serves to maximize the space available for clot removal. The valve 392 (wire 394, 412) or a valve formed by tube 422 and sleeve 424 in FIG. 42 regulates the flow of irrigation to optimize the clot removal procedures. These valves close the irrigation outlet or port during a clot-suctioning phase of an operating cycle and open the outlet after a proximally directed stroke of the cutter element.

Tubular member 364, 436, etc., particularly proximal portion 368, as well as drive rod 378 may be made with sufficiently thin walls so that the thrombectomy device is flexible.

Although the invention has been described in terms of particular embodiments and applications, one of ordinary skill in the art, in light of this teaching, can generate additional embodiments and modifications without departing from the spirit of or exceeding the scope of the claimed invention. For example, other configurations of the suction, irrigation and clot-intake ports and other clot cutting techniques will occur readily to those of ordinary skill in the art. These alternate configurations and cutting tools are considered to be equivalent to those disclosed specifically herein.

It is to be noted that a pressure sensor or other detector may be operatively connected to a suction line extending to the suction port of the clot removal device. Upon sensing a decrease in pressure, owing to the drawing of material into the clot intake port, the sensor automatically triggers a cutting and ejection phase of an operating cycle. Accordingly, the entire process may be automated (see discussion above with respect to FIG. 1 et seq.).

A device in accordance with the invention may be use in internal organs other than blood vessels or vascular prostheses to remove material other than blood clots. However, the device is particularly effective in performing thrombectomies and removing other semi-solid and viscous materials such as adipose tissue or intraocular material.

It is to be observed that an implanted prosthetic device such as a vascular bypass made of synthetic materials is considered to be a vascular organ for purposes of the invention. It is to be further observed that the cutting edges of cutter elements disclosed herein may be serrated or toothed, for facilitating the cutting operation. Of course, one or more guide wires may be necessary, as well as locking elements at the distal ends of the two tubular parts for coupling the parts to form a single member.

It is to be understood that the feeding of fluid to a tubular member of a thrombectomy or other medical device as described herein operates to relieve negative pressure which is generated on an upstream side of a clot mass being sucked from the tubular member. With the clot-intake opening closed by the cutter element and the clot mass conforming in a liquid-tight or even an air-tight seal to the inner surface of the tubular member, an underpressure can be produced upstream of the clot mass, i.e., between the clot mass and the clot intake opening. This negative pressure so generated can be less than the negative pressure generated on a downstream side of the clot by the application of suction via the suction port. In this event, the clot mass can become stuck. The feeding of fluid (a gas such as or a liquid such as saline solution) to the tubular member on an upstream side thereof serves to relieve the underpressure on the upstream side of the severed clot mass and enable the production of a pressure gradient or differential which moves the severed clot mass synergistically along the tubular member to the suction port of the instrument assembly. This description of instrument operation is applicable to virtually all of the thrombectomy type devices disclosed herein, particularly including the devices of FIGS. 38–42.

It is to be noted further that the thrombectomy devices disclosed herein streamline a clot removal process in part by maximizing the amount of clot material which can be sucked into a suction channel of a thrombectomy device. This space efficiency is achieved in certain embodiments (FIGS. 25, 28, 37 and 38–42) by providing an irrigation channel and drive rod which are eccentrically located, against the wall of the tubular member. The eccentric disposition of the drive rod and irrigation channel maximizes the amount of clot that can be drawn into the instrument during each cycle of operation and ensures that a severed clot mass forms a seal with the inner surface of the tubular member, particularly along a distal end portion thereof. This seal enables the generation of the pressure gradient or differential referred to above.

Accordingly, it is to be understood that the drawings and descriptions herein are proffered by way of example to facilitate comprehension of the invention and should not be construed to limit the scope thereof.

What is claimed is:

1. A minimally invasive medical method, comprising:

providing a catheter, a tubular member and a drive rod, said catheter having a distal end section and a suction port, said tubular member having a distal end portion provided with an intake port and further having a outlet port, said drive rod being disposed in said tubular member and having a distal end provided with a cutter element having a cutting edge;

inserting said distal end section of said catheter into a patient;

inserting said tubular member into said catheter so that said intake port is disposed outside said catheter and said outlet port is disposed inside said catheter;

shifting said drive rod in said tubular member so that said cutter element moves to open said intake port;

applying suction to said catheter to pull material from the patient through said intake port into said distal end portion of said tubular member;

shifting said drive rod to move said cutting edge of said cutter element past said intake port to thereby sever the material pulled into said distal end portion of said tubular member;

by an application of suction force, drawing the severed material in a proximal direction from said distal end portion of said tubular member, through said outlet port and along said catheter, outside of said proximal portion of said tubular member, to said suction port of said catheter; and during the drawing of the severed material, feeding fluid into said tubular member upstream of said severed material to facilitate the drawing of the severed material.

2. The method defined in claim 1 wherein said drive rod has an irrigation port and wherein said drive rod is hollow, the feeding of said fluid to said tubular member including delivering said fluid through said drive rod to said irrigation port.

3. The method defined in claim 2, further comprising closing said irrigation port during the pulling of material through said intake port into said distal end portion of said tubular member, also comprising opening said irrigation outlet after the severing of the pulled-in material by said cutting edge.

4. The method defined in claim 3 wherein a valve is disposed in said distal end portion of said tubular member and wherein the closing and opening of said irrigation port are effectuated by operating said valve.

5. A minimally invasive medical method comprising:

providing a tubular member, said tubular member having a distal end portion provided with an intake port and a valve, said tubular member having a cutter element disposed inside said tubular member, said cutter element having a cutting edge;

inserting said tubular member into a patient;

applying suction to said tubular member to draw material from the patient into said tubular member through said intake port;

shifting said cutter element in said tubular member so that said cutting edge of said cutter element moves past said intake port to sever the drawn-in material;

applying suction to said tubular member to draw the severed material in a proximal direction through said tubular member; and operating said valve (a) to prevent flow of an irrigation fluid into said tubular member during application of suction to draw said material into said tubular member through said intake port and (b) to enable a feeding of said irrigation fluid into said tubular member upstream of said severed material during application of suction to draw said severed material through said tubular member.

6. The method defined in claim 5 wherein the shifting of said cutter element includes shifting a drive rod extending into said tubular member to said cutter element, said drive rod having a lumen and an irrigation outlet communicating with said lumen at a distal end thereof, further comprising feeding said irrigation fluid to said tubular member upstream of severed material via said lumen and said irrigation outlet.

7. A minimally invasive medical method comprising:

providing a tubular member, said tubular member having a distal end portion provided with an intake port and a one-way valve, a balloon being disposed on said tubular member, said tubular member having a cutter element disposed inside said tubular member, said cutter element having a cutting edge;

inserting said tubular member into a vascular component of a patient;

feeding a pressurization fluid to said distal end portion of said tubular member and from said distal end portion through said one-way valve to said balloon;

inflating said balloon in said vascular component by virtue of said feeding of said pressurization fluid;

after inflation of said balloon, exerting tension on said tubular member to pull said balloon through the patient;

applying suction to said tubular member to draw material from the patient into said tubular member through said intake port;

shifting said cutter element in said tubular member so that said cutting edge of said cutter element moves past said intake port to sever the drawn-in material;

applying suction to said tubular member to draw the severed clot material in a proximal direction through said tubular member; and subsequent to pulling of said balloon through said vascular component, shifting said cutter element in a distal direction to open said one-way valve and deflate said balloon.

8. A method for removing material from inside a patient, comprising:

providing a tubular member having a suction port and a distal end portion provided with an intake port;

inserting a portion of said tubular member through a skin surface of a patient and into an internal structure of the patient so that said suction port is located outside of the patient and said intake port is located in said internal structure;

upon completion of said inserting, applying suction to said tubular member via said suction port to thereby draw material in said internal structure towards said intake port;

upon a drawing of said material at least partially into said tubular member through said intake port, severing a portion of said material inside said tubular member;

upon the severing of said portion of said material, maintaining said intake port in a closed configuration;

by virtue of the closure of said intake port, generating a pressure gradient across the severed portion of said material inside said tubular member to move said severed portion along said tubular member to said suction port, the generating of said pressure gradient including applying suction to said tubular member via said suction port, the generating of said pressure gradient also including feeding fluid to said tubular member on a side of said severed portion opposite said suction port, thereby relieving negative pressure generated in said tubular member between said severed portion and said intake port owing to motion of said severed portion in response to suction from said suction port.

9. The method defined in claim 8 wherein said tubular member is provided internally with a drive rod and a cutter element, said a drive rod having a distal end connected to said cutter element, said drive rod being eccentrically disposed substantially inside said tubular member, the severing of said portion of material being implement by moving said drive rod to shift said cutter element, an irrigation port being disposed in said drive rod, the feeding of fluid to said tubular member including feeding said fluid through said drive rod to said irrigation port.

10. The method defined in claim 8 wherein the tubular member is provided with a movable or shiftable cutter element having a cutting edge, the severing of said portion of said material including shifting said cutter element so that said cutting edge moves past said intake port, the closing of said intake port including blocking said intake port with said cutter element.

\* \* \* \* \*